(12) United States Patent
Scott et al.

(10) Patent No.: US 7,635,541 B2
(45) Date of Patent: Dec. 22, 2009

(54) METHOD FOR CHARGING LITHIUM-ION BATTERY

(75) Inventors: Erik R. Scott, Maple Grove, MN (US); William G. Howard, Roseville, MN (US); Craig L. Schmidt, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 771 days.

(21) Appl. No.: 11/260,853

(22) Filed: Oct. 27, 2005

(65) Prior Publication Data

US 2006/0093894 A1   May 4, 2006

Related U.S. Application Data

(60) Provisional application No. 60/647,292, filed on Jan. 26, 2005, provisional application No. 60/624,075, filed on Oct. 29, 2004.

(51) Int. Cl.
*H01M 4/58* (2006.01)
*A61N 1/00* (2006.01)
*H02J 7/00* (2006.01)

(52) U.S. Cl. ............... 429/231.95; 429/231.5; 607/2; 607/9; 607/116; 607/137; 320/137

(58) Field of Classification Search ............ 429/218.1, 429/223, 224, 231.5, 231.95; 607/2, 9, 41, 607/116, 137; 320/162, 137
See application file for complete search history.

(56) References Cited

U.S. PATENT DOCUMENTS

| | | | |
|---|---|---|---|
| 3,791,867 A | 2/1974 | Broadhead et al. | |
| 3,864,167 A | 2/1975 | Broadhead et al. | |
| 3,898,096 A | 8/1975 | Herédy et al. | |
| 4,009,052 A | 2/1977 | Whittingham | |
| 4,048,397 A | 9/1977 | Rothbauer | |
| 4,049,887 A | 9/1977 | Whittingham | |
| 4,113,921 A | 9/1978 | Goldstein et al. | |
| 4,194,062 A | 3/1980 | Carides et al. | |
| 4,202,702 A | 5/1980 | Nuss | |
| 4,340,652 A | 7/1982 | Raistrick et al. | |

(Continued)

FOREIGN PATENT DOCUMENTS

EP   0 567 149 B1   10/1993

(Continued)

OTHER PUBLICATIONS

Request for Continued Examination (RCE) and Reply and Amendment for U.S. Appl. No. 10/979,040, filed with the USPTO on Dec. 11, 2008, 16 pages.

(Continued)

*Primary Examiner*—Patrick Ryan
*Assistant Examiner*—Thomas H. Parsons
(74) *Attorney, Agent, or Firm*—Scott A. Marks; Stephen W. Bauer; Foley & Lardner LLP

(57) ABSTRACT

A method for charging an implantable medical device includes charging a lithium-ion battery provided in a medical device, the lithium-ion battery having a negative electrode with a lithium titanate active material. For at least a portion of the charging, the potential of the negative electrode is more than approximately 70 millivolts below the equilibrium potential of the negative electrode.

38 Claims, 10 Drawing Sheets

U.S. PATENT DOCUMENTS

| | | | |
|---|---|---|---|
| 4,446,212 A | 5/1984 | Kaun | |
| 4,464,447 A | 8/1984 | Lazzari et al. | |
| 4,507,371 A | 3/1985 | Thackeray et al. | |
| 4,547,442 A | 10/1985 | Besenhard et al. | |
| 4,555,456 A | 11/1985 | Kanehori et al. | |
| 4,668,595 A | 5/1987 | Yoshino et al. | |
| 4,764,437 A | 8/1988 | Kaun | |
| 4,830,939 A | 5/1989 | Lee et al. | |
| H723 H | 1/1990 | Plichta et al. | |
| 5,053,297 A | 10/1991 | Yamahira et al. | |
| 5,077,151 A | 12/1991 | Yasuda et al. | |
| 5,147,737 A | 9/1992 | Post et al. | |
| 5,147,739 A | 9/1992 | Beard | |
| 5,160,712 A | 11/1992 | Thackeray et al. | |
| 5,162,170 A | 11/1992 | Miyabayashi et al. | |
| 5,169,736 A | 12/1992 | Bittihn et al. | |
| 5,176,969 A | 1/1993 | Miyabayashi et al. | |
| 5,187,033 A | 2/1993 | Koshiba | |
| 5,187,035 A | 2/1993 | Miyabayashi et al. | |
| 5,196,279 A | 3/1993 | Tarascon | |
| 5,264,201 A | 11/1993 | Dahn et al. | |
| 5,284,721 A | 2/1994 | Beard | |
| 5,296,318 A | 3/1994 | Gozdz et al. | |
| 5,300,373 A | 4/1994 | Shackle | |
| 5,322,746 A | 6/1994 | Wainwright | |
| 5,340,666 A | 8/1994 | Tomantschger et al. | |
| 5,401,598 A | 3/1995 | Miyabayashi et al. | |
| 5,411,537 A * | 5/1995 | Munshi et al. | 607/33 |
| 5,418,090 A | 5/1995 | Koksbang et al. | |
| 5,498,489 A | 3/1996 | Dasgupta et al. | |
| 5,510,212 A | 4/1996 | Delnick et al. | |
| 5,525,441 A | 6/1996 | Reddy et al. | |
| 5,545,468 A | 8/1996 | Koshiba et al. | |
| 5,547,785 A | 8/1996 | Yumiba et al. | |
| 5,569,553 A | 10/1996 | Smesko et al. | |
| 5,576,608 A * | 11/1996 | Nagai et al. | 320/159 |
| 5,652,072 A | 7/1997 | Lamanna et al. | |
| 5,670,862 A | 9/1997 | Lewyn | |
| 5,691,081 A | 11/1997 | Krause et al. | |
| 5,744,264 A | 4/1998 | Barker | |
| 5,776,628 A | 7/1998 | Kraft et al. | |
| 5,882,218 A | 3/1999 | Reimers | |
| 5,888,665 A | 3/1999 | Bugga et al. | |
| 5,911,947 A | 6/1999 | Mitchell | |
| 5,935,724 A | 8/1999 | Spillman et al. | |
| 5,935,728 A | 8/1999 | Spillman et al. | |
| 5,968,681 A | 10/1999 | Miura et al. | |
| 6,001,507 A | 12/1999 | Ono et al. | |
| 6,007,947 A | 12/1999 | Mayer | |
| 6,025,093 A | 2/2000 | Herr | |
| 6,060,186 A | 5/2000 | Broussely et al. | |
| 6,120,938 A | 9/2000 | Atsumi et al. | |
| 6,139,815 A | 10/2000 | Atsumi et al. | |
| 6,165,638 A | 12/2000 | Spillman et al. | |
| 6,171,729 B1 | 1/2001 | Gan et al. | |
| 6,203,947 B1 | 3/2001 | Peled et al. | |
| 6,203,994 B1 | 3/2001 | Epps et al. | |
| 6,207,327 B1 | 3/2001 | Takada et al. | |
| 6,221,531 B1 | 4/2001 | Vaughey et al. | |
| 6,228,536 B1 | 5/2001 | Wasynczuk | |
| 6,258,473 B1 | 7/2001 | Spillman et al. | |
| 6,265,100 B1 | 7/2001 | Saaski et al. | |
| 6,274,271 B1 | 8/2001 | Koshiba et al. | |
| 6,287,721 B1 | 9/2001 | Xie et al. | |
| 6,316,145 B1 | 11/2001 | Kida et al. | |
| 6,335,115 B1 | 1/2002 | Meissner | |
| 6,372,384 B1 | 4/2002 | Fujimoto et al. | |
| 6,379,842 B1 | 4/2002 | Mayer | |
| 6,451,480 B1 | 9/2002 | Gustafson et al. | |
| 6,453,198 B1 | 9/2002 | Torgerson et al. | |
| 6,461,751 B1 | 10/2002 | Boehm et al. | |
| 6,461,757 B1 | 10/2002 | Sasayama et al. | |
| 6,475,673 B1 | 11/2002 | Yamawaki et al. | |
| 6,489,062 B1 | 12/2002 | Watanabe | |
| 6,528,208 B1 | 3/2003 | Thackeray et al. | |
| 6,553,263 B1 | 4/2003 | Meadows et al. | |
| 6,596,439 B1 | 7/2003 | Tsukamoto et al. | |
| 6,645,675 B1 | 11/2003 | Munshi | |
| 6,677,083 B2 | 1/2004 | Suzuki et al. | |
| 6,706,445 B2 | 3/2004 | Barker et al. | |
| 6,720,112 B2 | 4/2004 | Barker et al. | |
| 6,730,437 B2 | 5/2004 | Leising et al. | |
| 6,737,191 B2 | 5/2004 | Gan et al. | |
| 6,759,168 B2 | 7/2004 | Yamasaki et al. | |
| 6,761,744 B1 | 7/2004 | Tsukamoto et al. | |
| 6,777,132 B2 | 8/2004 | Barker et al. | |
| 6,824,920 B1 | 11/2004 | Iwamoto et al. | |
| 6,849,360 B2 | 2/2005 | Marple | |
| 6,942,949 B2 | 9/2005 | Besenhard et al. | |
| 7,029,793 B2 | 4/2006 | Nakagawa et al. | |
| 7,101,642 B2 | 9/2006 | Tsukamoto et al. | |
| 7,157,185 B2 | 1/2007 | Marple | |
| 7,191,008 B2 | 3/2007 | Schmidt et al. | |
| 7,211,350 B2 * | 5/2007 | Amatucci | 429/231.95 |
| 7,337,010 B2 | 2/2008 | Howard et al. | |
| 7,459,235 B2 * | 12/2008 | Choi et al. | 429/217 |
| 2001/0008725 A1 | 7/2001 | Howard | |
| 2001/0012590 A1 | 8/2001 | Ehrlich | |
| 2001/0021472 A1 | 9/2001 | Barker et al. | |
| 2001/0031401 A1 | 10/2001 | Yamawaki et al. | |
| 2003/0025482 A1 | 2/2003 | Tsukamoto et al. | |
| 2003/0104282 A1 | 6/2003 | Xing et al. | |
| 2003/0157410 A1 | 8/2003 | Jarvis et al. | |
| 2003/0215716 A1 | 11/2003 | Suzuki et al. | |
| 2004/0023117 A1 | 2/2004 | Imachi et al. | |
| 2004/0096745 A1 | 5/2004 | Shibano et al. | |
| 2004/0147971 A1 | 7/2004 | Greatbatch et al. | |
| 2004/0147972 A1 | 7/2004 | Greatbatch et al. | |
| 2004/0158296 A1 | 8/2004 | Greatbatch et al. | |
| 2004/0168307 A1 | 9/2004 | Hong | |
| 2004/0176818 A1 | 9/2004 | Wahlstrand et al. | |
| 2004/0197657 A1 | 10/2004 | Spitler et al. | |
| 2005/0031919 A1 | 2/2005 | Ovshinsky et al. | |
| 2005/0069777 A1 | 3/2005 | Takami et al. | |
| 2005/0130043 A1 | 6/2005 | Gao et al. | |
| 2005/0147889 A1 | 7/2005 | Ohzuku et al. | |
| 2005/0164082 A1 | 7/2005 | Kishi et al. | |
| 2005/0244716 A1 | 11/2005 | Ogawa et al. | |
| 2006/0024582 A1 | 2/2006 | Li et al. | |
| 2006/0046149 A1 | 3/2006 | Yong et al. | |
| 2006/0068282 A1 | 3/2006 | Kishi et al. | |
| 2006/0093871 A1 | 5/2006 | Howard et al. | |
| 2006/0093872 A1 | 5/2006 | Howard et al. | |
| 2006/0093873 A1 | 5/2006 | Howard et al. | |
| 2006/0093894 A1 | 5/2006 | Scott et al. | |
| 2006/0093913 A1 | 5/2006 | Howard et al. | |
| 2006/0093916 A1 | 5/2006 | Howard et al. | |
| 2006/0093917 A1 | 5/2006 | Howard et al. | |
| 2006/0093918 A1 | 5/2006 | Howard et al. | |
| 2006/0093921 A1 | 5/2006 | Scott et al. | |
| 2006/0093923 A1 | 5/2006 | Howard et al. | |
| 2006/0095094 A1 | 5/2006 | Howard et al. | |
| 2006/0216612 A1 | 9/2006 | Jambunathan et al. | |
| 2006/0234125 A1 | 10/2006 | Valle | |
| 2006/0251968 A1 | 11/2006 | Tsukamoto et al. | |
| 2007/0009801 A1 | 1/2007 | Inagaki et al. | |
| 2007/0059587 A1 | 3/2007 | Kishi et al. | |
| 2007/0072085 A1 | 3/2007 | Chen et al. | |
| 2007/0077496 A1 | 4/2007 | Scott et al. | |
| 2007/0111099 A1 | 5/2007 | Nanjundaswamy et al. | |
| 2007/0134556 A1 | 6/2007 | Sano et al. | |
| 2007/0162083 A1 | 7/2007 | Schmidt et al. | |
| 2007/0233195 A1 | 10/2007 | Wahlstrand et al. | |
| 2007/0239221 A1 | 10/2007 | Kast et al. | |

| | | | |
|---|---|---|---|
| 2007/0248881 A1 | 10/2007 | Scott et al. | |
| 2007/0284159 A1 | 12/2007 | Takami et al. | |
| 2008/0020278 A1 | 1/2008 | Schmidt et al. | |
| 2008/0020279 A1 | 1/2008 | Schmidt et al. | |
| 2008/0026297 A1 | 1/2008 | Chen et al. | |
| 2008/0044728 A1 | 2/2008 | Schmidt et al. | |
| 2009/0035662 A1 | 2/2009 | Scott et al. | |

FOREIGN PATENT DOCUMENTS

| | | |
|---|---|---|
| EP | 0 732 761 A2 | 9/1996 |
| EP | 0 982 790 A1 | 3/2000 |
| EP | 1 014 465 A1 | 6/2000 |
| EP | 1 018 773 A1 | 7/2000 |
| EP | 1 069 635 A1 | 1/2001 |
| EP | 1 282 180 A1 | 2/2003 |
| EP | 1 487 039 A1 | 12/2004 |
| EP | 1 722 439 A1 | 11/2006 |
| JP | 56-136462 | 10/1981 |
| JP | 57-11476 | 1/1982 |
| JP | 63-1708 | 1/1982 |
| JP | 57-152669 | 9/1982 |
| JP | 02-309568 | 12/1990 |
| JP | 6-275263 | 9/1994 |
| JP | 10-027626 A | 1/1998 |
| JP | 2000156229 A | 6/2000 |
| JP | 2000-195499 | 7/2000 |
| JP | 2001-126756 | 5/2001 |
| JP | 2001-185141 A | 7/2001 |
| WO | WO 97/06569 A1 | 2/1997 |
| WO | WO 97/48141 | 12/1997 |
| WO | WO 00/017950 | 3/2000 |
| WO | WO 02/09215 A2 | 1/2002 |
| WO | WO 02/21628 A1 | 3/2002 |
| WO | WO 02/069414 A2 | 9/2002 |
| WO | WO 02/095845 A1 | 11/2002 |
| WO | WO 03/044880 A1 | 5/2003 |
| WO | WO 03/075371 A2 | 9/2003 |
| WO | WO 03/090293 A2 | 10/2003 |
| WO | WO 2006/050022 A2 | 5/2006 |
| WO | WO 2006/050023 A2 | 5/2006 |
| WO | WO 2006/050098 A1 | 5/2006 |
| WO | WO 2006/050099 A1 | 5/2006 |
| WO | WO 2006/050100 A2 | 5/2006 |
| WO | WO 2006/050117 A1 | 5/2006 |
| WO | WO 2006/050117 A2 | 5/2006 |
| WO | WO 2006/064344 A2 | 6/2006 |

OTHER PUBLICATIONS

Request for Continued Examination (RCE), Reply and Amendment and Terminal Disclaimers for U.S. Appl. No. 10/978,712, filed with the USPTO on Dec. 8, 2008, 20 pages.
U.S. Appl. No. 12/112,979, filed Apr. 30, 2008, Scott et al.
U.S. Appl. No. 12/240,652, filed Sep. 29, 2008, Scott et al.
Peramunage et al., Preparation of Micro-Sized $Li_4Ti_5O_{12}$ and Its Electrochemistry in Polyacrylonitrile Electrolye-Based Lithium Cells, Technical Papers, Electrochemical Science and Technology, J. Electrochem Soc., vol. 145, No. 8, Aug. 1998 © The Electrochemical Society, Inc., 7 pages.
Ohzuku et al., Zero-Strain Insertion Material of $Li[Li_{1/3}Ti_{5/3}]O_4$ for Rechargeable Lithium Cells, Electrochemical Science and Technology, J. Electrochem Soc., vol. 142, No. 5, May 1995 © The Electrochemical Society, Inc., 5 pages.
International Search Report for PCT/US2005/038970, date of mailing Oct. 25, 2006, 3 pages.
International Search Report for PCT/US2005/038761, date of mailing Oct. 4, 2006, 2 pages.
International Search Report for PCT/US2005/038762, date of mailing Oct. 2, 2006, 2 pages.
Non-Final Office Action for U.S. Appl. No. 10/979,040, filed Jan. 12, 2009, 10 pages.
Non-Final Office Action for U.S. Appl. No. 10/978,712, filed Jan, 5, 2009, 16 pages.

Scrosati, "Low Voltage Lithium-Ion Cells", Advances in Lithium-Ion Batteries Kluwer Academic/Plenum Publishers, pp. 289-308.
Nakahara, et al. "Preparation of Particulate $Li_4Ti_5O_{12}$ Having Excellent Characteristics As An Electrode Active Material For Power Storage Cells", Journal of Power Sources, 117, 2003, pp. 131-136.
Sawai, et al. "Factors Affecting Rate Capability of a Lithium-Ion Battery with $Li[Li_{1/3}Ti_{5/3}]O_4$ and $LiCo_{1/2}Ni_{1/2}O_2$", Abs. 75, $205^{th}$ Meeting, (1 page).
Kavan et al. "Proof of Concept—$Li_4Ti_5O_{12}$", Elecrochem. and Solid State Lett. 2002, 5, A39-A42, (p. 13).
Wang et al. "Novel Electrolytes for Nanocrystalline $Li_4Ti_5O_{12}$ Based High Power Lithium Ion Batteries".
International Search Report for PCT/US2005/038942, date of mailing, Mar. 2, 2006, 3 pages.
International Search Report for PCT/U52005/038943, date of mailing, Mar. 16, 2006, 3 pages.
International Search Report for PCT/US2005/038944, date of mailing, Mar. 31, 2006, 3 pages.
Murphy et al., Ternary $Li_xTiO_2$ Phases from Insertion Reactions, Solid State Ionics, vols. 9 & 10, 1983 © North-Holland Publishing Company, pp. 413-418.
Sasaki et al., Layered Hydrous Titanium Dioxide: Potassium Ion Exchange and Structural Characterization, Inorganic Chemistry, vol. 24, No. 14, © 1985 American Chemical Society, pp. 2265-2271.
Colbow et al., Structure and Electrochemistry of the Spinel Oxides $LiTi_2O_4$ and $Li_{4/3}Ti_{5/3}O_4$, Journal of Power Sources, vol. 26, 1989, © Elsevier Sequoia, pp. 397-402.
Brohan et al., Properties Physiques Des Bronzes $M_xTiO_2(B)$, Solid State Ionics, vols. 9 and 10, 1983, © North Holland Publishing Company, pp. 419-424.
Murphy et al., "Topochemical Reactions of Rutile Related Structures with Lithium", Mat. Res. Bull, vol. 13, No. 12, 1978, © Pergamon Press, Inc., pp. 1395-1402.
Wang et al., Li Insertion and Ion Exchange Reactions in the Ionic Conducting Tl2(M,Ti)8O16 Phases with Hollandite-Type Structure, Technical Papers, Solid-State Science and Technology, J. Electrochem Soc., vol. 138, No. 1, Jan. 1991, © The Electrochemical Society, Inc.
Sawai, et al., Factors Affecting Rate Capability of a Lithium-ion Battery with $Li[Li_{1/3}Ti_{5/3}]O_4$ and $LiCo_{1/2}Ni_{1/2}O_2$, Abs. 75, $205^{th}$ Meeting, 1 page.
Kavan, et al., Proof of Concept —$Li_4Ti_5O_{12}$, Electrochemical and Solid State Letters, 2002, vol. 5, A39-A42, p. 13.
Wang et al., Novel Eletrolytes for Nanocrystalline $Li_4Ti_5O_{12}$ Based High Power Lithium Ion Batteries.
Dahn et al., "Combinatorial Study of Sn1-xCox (0<x<0.6) and [Sn0.55Co0.45]1-yCy (0<y<0.5) Alloy Negative Electrode Materials for Li-Ion Batteries," Journal of Electrochemical Society, vol. 153, 2006, pp. A361-A365.
Fauteux et al., "Rechargeable lithium battery anodes: alternatives to metallic lithium," Journal of Applied Electrochemistry, vol. 23, 1993, pp. 1-10.
Guyomard et al., "New amorphous oxides as high capacity negative electrodes for lithium6 batteries the LixMV04 (M=Ni, Co, Cd, Zn; 1 <x<8) series," Journal of Power Sources, vol. 68, 1997, pp. 692-697.
Linden, David, Editor in Chief, Handbook of Batteries, Second Edition, McGraw-Hill, NY, 1995, 6 pages.
Ohzuku et al., "Why transition metal (di)oxides are the most attractive materials for batteries," Solid State Ionics, vol. 69, 1994, pp. 201-211.
Poizot et al., "Nano-sized transition-metal oxides as negative-electrode materials for lithium-ion batteries," Nature, vol. 407, 2000, cover and pp. 496-499.
Trifonova et al., "Sn-Sb and Sn-Bi Alloys as Anode Materials for Lithium-Ion Batteries," Ionics, vol. 8, 2002, cover and pp. 321-328.
Winter et al., "Insertion Electrode Materials for Rechargeable Lithium Batteries," Advanced Materials, vol. 10, 1998, pp. 725-763.
Winter et al., "Electrochemical lithiation of tin and tin-based intermetallics and composites," Electrochimica Acta, vol. 45, 1999, pp. 31-50.
Preliminary Amendment for U.S. Appl. No. 10/978,712, filed Oct. 29, 2004, 11 pages.

Non-Final Office Action for U.S. Appl. No. 10/978,712, filed Apr. 10, 2008, 12 pages.
Reply and Amendment and Declaration Under 1.131 for U.S. Appl. No. 10/978,712, filed with the USPTO on Jul. 16, 2008, 36 pages.
Final Office Action for U.S. Appl. No. 10/978,712, filed Oct. 9, 2008, 7 pages.
Preliminary Amendment for U.S. Appl. No. 10/979,040, filed Mar. 4, 2005, 11 pages.
Non-Final Office Action for U.S. Appl. No. 10/979,040, filed Apr. 2. 2008, 8 pages.
Reply and Amendment and Declaration under 1.131 for U.S. Appl. No. 10/979,040, filed with the USPTO on Jul. 16, 2008, 33 pages.
Final Office Action for U.S. Appl. No. 10/979,040, filed Sep. 19, 2008, 10 pages.
International Search Report and Written Opinion for Application No. PCT/US2008/066809, mailing date Oct. 29, 2008, 8 pages.
International Search Report and Written Opinion for Application No. PCT/US2008/066801, mailing date Oct. 29, 2008, 10 pages.
International Search Report and Written Opinion for Application No. PCT/US2008/066803, date of mailing Oct. 7, 2008, 12 pages.
International Search Report and Written Opinion for Application No. PCT/US2008/082598, date of mailing Feb. 18, 2009, 11 pages.
Reply and Amendment for U.S. Appl. No. 10/979,040, filed with the USPTO on Mar. 24, 2009, 12 pages.
Reply and Amendment for U.S. Appl. No. 10/978,712, filed with the USPTO on Mar. 24, 2009, 16 pages.
Final Office Action for U.S. Appl. No. 10/979,040, filed Jun. 16, 2009, 10 pages.
Final Office Action for U.S. Appl. No. 10/978,712, filed Jun. 17, 2009, 11 pages.
Ohzuku, Extended Abstracts from the Seventh Int'l Meeting on Li Batteries, Boston, MA, May 15-20, 1994, pp. 111-112.
Ohzuku, et al, "Zero-Strain Insertion Material of Li[Li$_{1/3}$Ti$_{5/3}$]O$_4$ for Rechargeable Lithium Cells", J. Electrochem. Soc. vol. 142 #5, 1995, pp. 1431-1435.
Ferg et al, "Spinel Anodes for Lithium-Ion Batteries", J. Electrochem. Soc. vol. 141 #11, 1994, pp. L147-L150.
Zaghib, et al, "Electrochemical Study of Li$_4$Ti$_5$O$_{12}$ As Negative Electrode for Li-Ion Polymer Rechargeable Batteries", Journal of Power Sources, 81-82, 1999, pp. 300-305.
Jansen, et. al., "Development of a High-Power Lithium-Ion Battery", Journal of Power Sources, 81-82, 1999, pp. 902-905.

Ariyoshi, et al., "Three-Volt Lithium-Ion Battery with Li[Ni$_{1/2}$Mn$_{3/2}$]O$_4$ and the Zero-Strain Insertion Material of Li[Li$_{1/3}$Ti$_{5/3}$]O$_4$,", Journal of Power Sources, 119-121, 2003, pp. 959-963.
Singhal, et al. "Nanostructured Electrodes for Next Generation Rechargeable Electrochemical Devices", Journal of Power Sources, 129, 2004, pp. 38-44.
FMC Lithium, CAS No. 74389-93-2, "Stabilized Lithium Metal Powder" Product Specification, Copyright 2001 FMC Corporation (2 pages).
Jarvis et al., "A Li-Ion Cell Containing a Non-Lithiated Cathode", Abs. 182, IMLB 12 Meeting (1 page), 2004.
Ohzuku et al., "Lithium-Ion Batteries of Li[Li$_{1/3}$Ti$_{5/3}$]O$_4$ With Selected Positive-Electrode Materials for Long-Life Power Application", Abs. 23, IMLB 12 Meeting (1 page), 2004.
New Li$_4$Ti$_5$O$_{12}$ Anode Material of Süd-Chemie AG for Lithium Ion Batteries, Süd-Chemie EXM 1037—Li$_4$Ti$_5$O$_{12}$, Product Specification (2 pages).
"Battery Materials—Ceramic Anode Material for 2.4 V Lithium-Ion Batteries"—EXM 1037—Li$_4$Ti$_5$O$_{12}$ (1 page), available at least by Oct. 25, 2004.
Guerfi, et. al., "Nano Electronically Conductive Titanium-Spinel as Lithium Ion Storage Negative Electrode", Journal of Power Sources, 126, 2004, pp. 163-168.
Prosini, et. al., "Li$_4$Ti$_5$O$_{12}$ As Anode In All-Solid-State, Plastic, Lithium-Ion Batteries for Low-Power Applications" Solid State Ionics, 144, 2001, pp. 185-192.
Cava et al., The Crystal Structures of the Lithium-Inserted Metal Oxides Li0.5TiO$_2$Anatase, LiTi204 Spinel, and L$_2$Ti$_2$O$_4$, Journal of Solid State Chemistry, vol. 53, Jan. 1984 © Academic Press, inc., pp. 64-75..
Murphy et al., Lithium Insertion in Anatase: A New Route to the Spinel LiTi$_{204}$, Revue De Chimie Minerale, vol. 19, 1982, 9 pgs.
Mikula et al., Photoelectrochemical Properties of Anodic TiO$_2$ Layers Prepared by Various Current Densities, J. Electrochemical Society, Vol. 139, No. 12, Dec. 1992 © The Electrochemical Society, Inc., pp. 3470-3474.
Murphy et al., Ternary Li$_x$TiO$_2$ Phases from Insertion Reactions, Solid State Ionics, vols. 9 & 10, 1983 © North-Holland Publishing Company, pp. 413-418.

* cited by examiner

A. Cell Voltage

B. Charge Current

C. Negative Electrode Potential

D. Charge Time

METHOD FOR CHARGING LITHIUM-ION BATTERY

CROSS-REFERENCE TO RELATED APPLICATIONS

This Application claims the benefit under 35 U.S.C. § 119(e) of U.S. Provisional Patent Application No. 60/624,075 filed Oct. 29, 2004 and U.S. Provisional Patent Application No. 60/647,292 filed Jan. 26, 2005, each of which is incorporated herein by reference in its entirety.

BACKGROUND

The present invention relates generally to the field of lithium-ion batteries. Specifically, the present invention relates to lithium-ion batteries may be charged at an overpotential to increase the speed of charging.

Lithium-ion batteries include a positive current collector (e.g., aluminum such as an aluminum foil) having an active material provided thereon (e.g., $LiCoO_2$) and a negative current collector (e.g., copper such as a copper foil) having an active material (e.g., a carbonaceous material such as graphite) provided thereon. Together the positive current collector and the active material provided thereon are referred to as a positive electrode, while the negative current collector and the active material provided thereon are referred to as a negative electrode.

FIG. 1 shows a schematic representation of a portion of a lithium-ion battery 10 such as that described above. The battery 10 includes a positive electrode 20 that includes a positive current collector 22 and a positive active material 24, a negative electrode 30 that includes a negative current collector 32 and a negative active material 34, an electrolyte material 40, and a separator (e.g., a polymeric microporous separator, not shown) provided intermediate or between the positive electrode 20 and the negative electrode 30. The electrodes 20, 30 may be provided as relatively flat or planar plates or may be wrapped or wound in a spiral or other configuration (e.g., an oval configuration). The electrode may also be provided in a folded configuration.

During charging and discharging of the battery 10, lithium ions move between the positive electrode 20 and the negative electrode 30. For example, when the battery 10 is discharged, lithium ions flow from the negative electrode 30 to the positive electrode 20. In contrast, when the battery 10 is charged, lithium ions flow from the positive electrode 20 to the negative electrode 30.

FIG. 2 is a graph 100 illustrating the theoretical charging and discharging behavior for a conventional lithium-ion battery. Curve 110 represents the electrode potential for a positive electrode that includes an aluminum current collector having a $LiCoO_2$ active material provided thereon, while curve 120 represents the electrode potential for a negative electrode that includes a copper current collector having a carbonaceous active material provided thereon. The difference between curves 110 and 120 is representative of the overall cell voltage.

As shown in FIG. 2, upon initial charging to full capacity, the potential of the positive electrode, as shown by curve 110, increases from approximately 3.0 volts to a point above the corrosion potential of copper used to form the negative electrode (designated by dashed line 122). The potential of the negative electrode decreases from approximately 3.0 volts to a point below the decomposition potential of the $LiCoO_2$ active material provided on the aluminum current collector (designated by dashed line 112). Upon initial charging, the battery experiences an irreversible loss of capacity due to the formation of a passive layer on the negative current collector, which may be referred to as a solid-electrolyte interface ("SEI"). The irreversible loss of capacity is shown as a ledge or shelf 124 in curve 120.

One difficulty with conventional lithium-ion batteries is that when such a battery is discharged to a point near zero volts, it may exhibit a loss of deliverable capacity and corrosion of the negative electrode current collector (copper) and possibly of the battery case, depending on the material used and the polarity of the case. As shown in FIG. 2, after initial charging of the battery, a subsequent discharge of the battery in which the voltage of the battery approaches zero volts (i.e., zero percent capacity) results in a negative electrode potential that follows a path designated by dashed line 126. As shown in FIG. 2, the negative electrode potential levels off or plateaus at the copper corrosion potential of the negative current collector (approximately 3.5 volts for copper and designated by dashed line 122 in FIG. 2).

During charging of a conventional lithium-ion battery, it may be necessary to take certain precautions to avoid plating of lithium on the negative electrode. For example, as shown in FIG. 2, the potential of the negative electrode (shown as curve 120) approaches a level of approximately 0.1 volts with increasing capacity during charging. For this reason, during charging of conventional lithium-ion batteries, a "taper charge" is applied as the battery approaches a full charge condition to avoid a situation in which the potential of the negative electrode falls below approximately 0.1 volts. With a taper charge, the charging voltage is decreased as the battery approaches a full charge condition to minimize the risk that lithium will be plated on the negative electrode. Further, because of the relatively low potential of the negative electrode, it has been conventionally believed that charge voltages significantly greater than the open circuit voltage of the battery may not be used in charging the battery. As a result, the speed of charging of conventional lithium-ion batteries may not proceed as rapidly as may be desired.

The medical device industry produces a wide variety of electronic and mechanical devices for treating patient medical conditions. Depending upon the medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life.

It may be desirable to provide a source of battery power for such medical devices, including implantable medical devices. In such cases, it may be advantageous to provide a battery that may be recharged relatively quickly such that inconvenience to the patient may be reduced. It would also be advantageous to provide a battery that may be charged at a greater rate than conventional lithium-ion batteries without significant risk of plating lithium on the negative electrode of the battery. It would also be advantageous to provide a medical device (e.g., an implantable medical device) that utilizes such a battery.

SUMMARY

An exemplary embodiment of the present invention relates to a method for charging an implantable medical device. The method includes charging a lithium-ion battery provided in a medical device, the lithium-ion battery having a negative electrode with a lithium titanate active material. For at least a portion of the charging, the potential of the negative electrode is more than approximately 70 millivolts below the equilibrium potential of the negative electrode.

Another exemplary embodiment of the present invention relates to a method of charging a lithium-ion battery that includes charging a lithium-ion battery in a charging operation, the lithium-ion battery including a negative electrode that comprises a lithium titanate material. For at least a portion of the charging operation the overpotential of the negative electrode is greater than approximately 70 millivolts. The lithium battery is included in an implantable medical device and the charging operation does not result in lithium plating at the negative electrode.

Another exemplary embodiment of the present invention relates to a method of charging a lithium-ion battery that includes inductively charging a lithium-ion battery according to a charging routine that provides an overpotential of at least 70 millivolts to a negative electrode of the battery for at least a portion of the charging routine, the lithium-ion battery comprising a lithium titanate negative active material.

DETAILED DESCRIPTION

Figure 3:
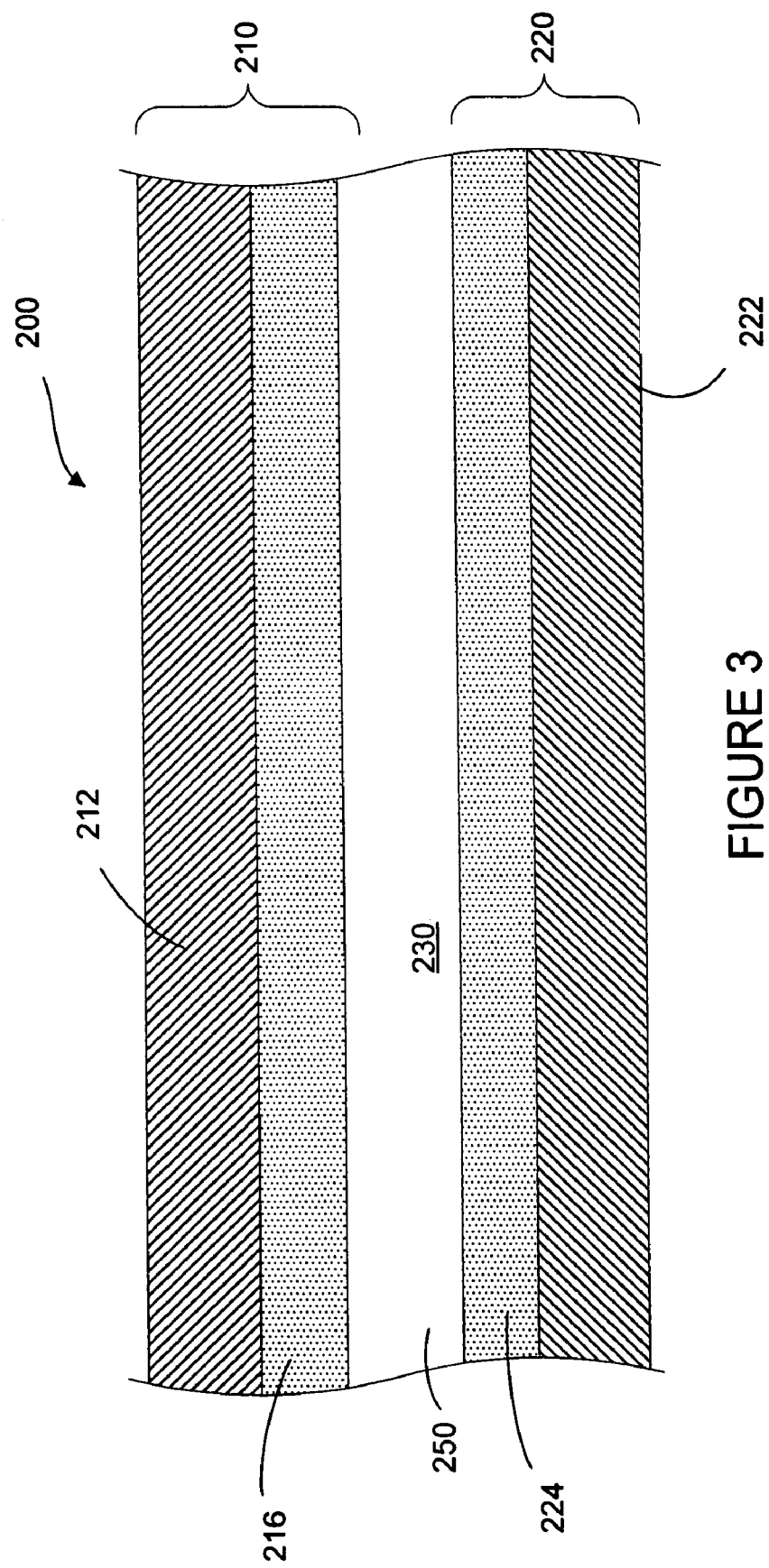
FIG. 3 is a schematic cross-sectional view of a portion of a lithium-ion battery according to an exemplary embodiment.

With reference to FIG. 3, a schematic cross-sectional view of a portion of a lithium-ion battery 200 is shown according to an exemplary embodiment. According to an exemplary embodiment, the battery 200 has a rating of between approximately 1 and 1000 milliampere hours (mAh). According to another exemplary embodiment, the battery has a rating of between approximately 100 and 400 mAh. According to another exemplary embodiment, the battery is an approximately 300 mAh battery. According to another exemplary embodiment, the battery is an approximately 75 mAh battery.

The battery 200 includes at least one positive electrode 210 and at least one negative electrode 220. The electrodes may be provided as flat or planar components of the battery 200, may be wound in a spiral or other configuration, or may be provided in a folded configuration. For example, the electrodes may be wrapped around a relatively rectangular mandrel such that they form an oval wound coil for insertion into a relatively prismatic battery case. According to other exemplary embodiments, the battery may be provided as a button cell battery, a thin film solid state battery, or as another lithium-ion battery configuration.

The battery case (not shown) may be made of a metal such as aluminum or an aluminum alloy or another metal. According to an exemplary embodiment, the battery case may be made of titanium, a titanium alloy, or stainless steel. According to another exemplary embodiment, the battery case may be made of a plastic material or a plastic-foil laminate material (e.g., an aluminum foil provided intermediate a polyolefin layer and a polyester layer).

According to an exemplary embodiment, the negative electrode is coupled to an aluminum case by a member or tab comprising aluminum or an aluminum alloy. An aluminum or aluminum alloy member or tab may be coupled or attached to the positive electrode. The tabs may serve as terminals for the battery according to an exemplary embodiment.

The dimensions of the battery 200 may differ according to a variety of exemplary embodiments. For example, according to one exemplary embodiment in which the electrodes are wound such that they may be provided in a relatively prismatic battery case, the battery has dimensions of between approximately 30-40 mm by between approximately 20-30 mm by between approximately 5-7 mm. According to another exemplary embodiment, the dimensions of the battery are approximately 20 mm by 20 mm by 3 mm. According to another exemplary embodiment, a battery may be provided in the form of a button cell type battery having a diameter of approximately 30 mm and a thickness of approximately 3 mm. It will be appreciated by those of skill in the art that such dimensions and configurations as are described herein are illustrative only, and that batteries in a wide variety of sizes, shapes, and configurations may be produced in accordance with the novel concepts described herein.

An electrolyte 230 is provided intermediate or between the positive and negative electrodes to provide a medium through which lithium ions may travel. The electrolyte may be a liquid (e.g., a lithium salt dissolved in one or more non-aqueous solvents). According to an exemplary embodiment, the electrolyte may be a mixture of propylene carbonate (PC), ethylene carbonate (EC), diethyl carbonate (DEC) and a 1.0 M salt of $LiPF_6$. According to another exemplary embodiment, an electrolyte may be used that does not use constituents that may commonly be used in lithium batteries (e.g., ethylene carbonate, vinylene carbonate, lithium bis-oxalatoborate salt (sometimes referred to as LiBOB), etc.).

Various other electrolytes may be used according to other exemplary embodiments. According to an exemplary embodiment, the electrolyte may be a lithium salt dissolved in a polymeric material such as poly(ethylene oxide) or silicone. According to another exemplary embodiment, the electrolyte may be an ionic liquid such as N-methyl-N-alkylpyrrolidinium bis(trifluoromethanesulfonyl)imide salts. According to another exemplary embodiment, the electrolyte may be a solid state electrolyte such as a lithium-ion conducting glass such as lithium phosphorous oxynitride (LiPON). According to another exemplary embodiment, the electrolyte may be a 1:1 mixture of ethylene carbonate to diethylene carbonate (EC:DEC) in a 1.0 M salt of $LiPF_6$. According to another exemplary embodiment, the electrolyte may include a polypropylene carbonate solvent and a lithium bis-oxalatoborate salt. According to other exemplary embodiments, the electrolyte may comprise one or more of a PVDF copolymer, a PVDF-polyimide material, and organosilicon polymer, a thermal polymerization gel, a radiation cured acrylate, a particulate with polymer gel, an inorganic gel polymer electrolyte, an inorganic gel-polymer electrolyte, a PVDF gel, polyethylene oxide (PEO), a glass ceramic electrolyte, phosphate glasses, lithium conducting glasses, lithium conducting ceramics, and an inorganic ionic liquid gel, among others.

A separator 250 is provided intermediate or between the positive electrode 210 and the negative electrode 220. According to an exemplary embodiment, the separator 250 is a polymeric material such as a polypropylene/polyethelene copolymer or another polyolefin multilayer laminate that includes micropores formed therein to allow electrolyte and lithium ions to flow from one side of the separator to the other. The thickness of the separator 250 is between approximately 10 micrometers (μm) and 50 μm according to an exemplary embodiment. According to a particular exemplary embodiment, the thickness of the separator is approximately 25 μm and the average pore size of the separator is between approximately 0.02 μm and 0.1 μm.

The positive electrode 210 includes a current collector 212 made of a conductive material such as a metal. According to an exemplary embodiment, the current collector 212 comprises aluminum or an aluminum alloy.

According to an exemplary embodiment, the thickness of the current collector 212 is between approximately 5 μm and 75 μm. According to a particular exemplary embodiment, the thickness of the current collector 212 is approximately 20 μm. It should also be noted that while the positive current collector 212 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

The current collector 212 has a layer of active material 216 provided thereon (e.g., coated on the current collector). While FIG. 3 shows that the active material 216 is provided on only one side of the current collector 212, it should be understood that a layer of active material similar or identical to that shown as active material 216 may be provided or coated on both sides of the current collector 212.

According to an exemplary embodiment, the active material 216 is a material or compound that includes lithium. The lithium included in the primary active material 216 may be doped and undoped during discharging and charging of the battery, respectively. According to an exemplary embodiment, the primary active material 216 is lithium cobalt oxide ($LiCoO_2$). According to another exemplary embodiment, the active material provided on the current collector 212 is $LiMn_2O_4$. According to another exemplary embodiment, the active material provided on the current collector 212 is a material of the form $LiCo_xNi_{(1-x)}O_2$, where x is between approximately 0.05 and 0.8. According to another exemplary embodiment, the active material provided on the positive current collector 212 is a material of the form $LiNi_xCo_y$-$MN_{(1-x-y)}O_2$ (e.g., $LiNi_{1/3}Co_{1/3}Mn_{1/3}O_2$). According to another exemplary embodiment, the active material provided on the current collector 212 is a metal-doped variety of one of these materials, such as a material of the form $LiM_xCo_y$-$Ni_{(1-x-y)}O_2$, where M is aluminum or titanium and x is between approximately 0.05 and 0.3 and y is between approximately 0.1 and 0.3.

For certain applications, it may be desirable to provide a battery having a cell voltage of greater than approximately 3 volts. In such cases, a higher-voltage active material may be utilized on the positive current collector, such as a material in the form $Li_{2-x}Co_yFe_zMn_{4-(y+z)}O_8$ (e.g., $Li_2Co_{0.4}Fe_{0.4}Mn_{3.2}O_8$). It is believed that such an active material may charge up to 5.2 volts versus a lithium reference electrode, making it possible to obtain an overall cell voltage of up to approximately 3.7 volts. Other relatively high-voltage active materials that may be used for the positive electrode include $LiCoPO_4$; $LiNiPO_4$; $Li2CoPO_4F$; $Li[Ni_{0.2}Li_{0.2}Mn_{0.6}]O_2$; and $LiCo_xMn_{2-x}O_4$ (e.g., $LiCo_{0.3}Mn_{1.7}O_4$).

According to various other exemplary embodiments, the active material may include a material such as a material of the form $Li_{1-x}MO_2$ where M is a metal (e.g., $LiCoO_2$, $LiNiO_2$, and $LiMnO_2$), a material of the form $Li_{1-w}(M'_xM''_y)O_2$ where M' and M'' are different metals (e.g., $Li(Cr_xMn_{1-x})O_2$, $Li(Al_xMn_{1-x})O_2$, $Li(Co_xM_{1-x})O_2$ where M is a metal, $Li(Co_xNi_{1-x})O_2$, and $Li(Co_xFe_{1-x})O_2$)), a material of the form $Li_{1-w}(Mn_xNi_yCo_z)O_2$ (e.g., $Li(Mn_{1/3}Ni_{1/3}Co_{1/3})O_2$, $Li(Mn_{1/3}Ni_{1/3}Co_{1/3-x}Mg_x)O_2$, $Li(Mn_{0.4}Ni_{0.4}Co_{0.2})O_2$, and $Li(Mn_{0.1}Ni_{0.1}Co_{0.8})O_2$), a material of the form $Li_{1-w}(Mn_xNi_xCo_{1-2x})O_2$, a material of the form $Li_{1-w}(Mn_xNi_yCo_zAl_w)O_2$, a material of the form $Li_{1-w}(Ni_xCo_yAl_z)O_2$ (e.g., $Li(Ni_{0.8}Co_{0.15}Al_{0.05})O_2$), a material of the form $Li_{1-w}(Ni_xCo_yM_z)O_2$ where M is a metal, a material of the form $Li_{1-w}(Ni_xMn_yM_z)O_2$ where M is a metal, a material of the form $Li(Ni_{x-y}Mn_yCr_{2-x})O_4$, $LiMn_2O_4$, a material of the form $LiM'M''_2O_4$ where M' and M'' are different metals (e.g., $LiMn_{2-y-z}Ni_yO_4$, $Li_zO_4$, $LiNiCuO_4$, $LiMn_{1-x}Al_xO_4$, $LiNi_{0.5}Ti_{0.5}O_4$, and $Li_{1.05}Al_{0.1}Mn_{1.85}O_{4-z}F_z$), $Li_2MnO_3$, a material of the form $Li_xV_yO_z$ (e.g., $LiV_3O_8$, $LiV_2O_5$, and $LiV_6O_{13}$), a material of the form $LiMPO_4$ where M is a metal or $LiM'_xM''_{1-x}PO_4$ where M' and M'' are different metals (e.g., $LiFePO_4$, $LiFe_xM_{1-x}PO_4$ where M is a metal, $LiVOPO_4$, and $Li_3V_2(PO_4)_3$, and $LiMPO_{4x}$, where M is a metal such as iron or vanadium and X is a halogen such as fluorine, and combinations thereof.

A binder material may also be utilized in conjunction with the layer of active material 216 to bond or hold the various electrode components together. For example, according to an exemplary embodiment, the layer of active material may include a conductive additive such as carbon black and a binder such as polyvinylidine fluoride (PVDF) or an elastomeric polymer.

According to an exemplary embodiment, the thickness of the layer of active material 216 is between approximately 0.1 μm and 3 mm. According to another exemplary embodiment, the thickness of the layer of active material 216 is between approximately 25 μm and 300 μm. According to a particular exemplary embodiment, the thickness of the layer of active material 216 is approximately 75 μm.

The negative electrode 220 includes a current collector 222 that is made of a conductive material such as a metal. According to an exemplary embodiment, the current collector 222 is aluminum or an aluminum alloy. One advantageous feature of utilizing an aluminum or aluminum alloy current collector is that such a material is relatively inexpensive and may be relatively easily formed into a current collector. Other advantageous features of using aluminum or an aluminum alloy includes the fact that such materials may have a relatively low density, are relatively highly conductive, are readily weldable, and are generally commercially available. According to another exemplary embodiment, the current collector 222 is titanium or a titanium alloy. According to another exemplary embodiment, the current collector 222 is silver or a silver alloy.

While the negative current collector 222 has been illustrated and described as being a thin foil material, the negative current collector may have any of a variety of other configurations according to various exemplary embodiments. For example, the positive current collector may be a grid such as a mesh grid, an expanded metal grid, a photochemically etched grid, or the like.

According to an exemplary embodiment, the thickness of the current collector 222 is between approximately 100 nm and 100 µm. According to another exemplary embodiment, the thickness of the current collector 222 is between approximately 5 µm and 25 µm. According to a particular exemplary embodiment, the thickness of the current collector 222 is approximately 10 µm.

The negative current collector 222 has an active material 224 provided thereon. While FIG. 3 shows that the active material 224 is provided on only one side of the current collector 222, it should be understood that a layer of active material similar or identical to that shown may be provided or coated on both sides of the current collector 222.

According to an exemplary embodiment, the negative active material 224 is a lithium titanate material such as $Li_4Ti_5O_{12}$ (sometimes referred to as $Li_{1+x}[Li_{1/3}Ti_{5/3}]O_4$, with $0 \leq x < 1$). Other lithium titanate materials which may be suitable for use as the negative active material may include one or more of the following lithium titanate spinel materials: $H_xLi_{y-x}TiO_xO_4$, $H_xLi_{y-x}TiO_xO_4$, $Li_4M_xTi_{5-x}O_{12}$, $Li_xTi_yO_4$, $Li_xTi_yO_4$, $Li_4[Ti_{1.67}Li_{0.33-y}M_y]O_4$, $Li_2TiO_3$, $Li_4Ti_{4.75}V_{0.25}O_{12}$, $Li_4Ti_{4.75}Fe_{0.25}O_{11.88}$, $Li_4Ti_{4.5}Mn_{0.5}O_{12}$, and LiM'M"XO_4 (where M' is a metal such as nickel, cobalt, iron, manganese, vanadium, copper, chromium, molybdenum, niobium, or combinations thereof, M" is an optional three valent non-transition metal, and X is zirconium, titanium, or a combination of these two). Note that such lithium titanate spinel materials may be used in any state of lithiation (e.g., $Li_{4+x}Ti_5O_{12}$, where $0 \geq x \geq 3$).

According to an exemplary embodiment, the lithium titanate may be provided such that at least five percent is in the form of lithium titanate nanoparticles (e.g., having a particle size of less than approximately 500 nanometers). The use of such nonoparticles is intended to provide greater surface area for doping and undoping of lithium ions.

A binder material may also be utilized in conjunction with the layer of active material 224. For example, according to an exemplary embodiment, the layer of active material may include a binder such as polyvinylidine fluoride (PVDF) or an elastomeric polymer. The active material 224 may also include a conductive material such as carbon (e.g., carbon black) at weight loadings of between zero and ten percent to provide increased electronic conductivity.

According to various exemplary embodiments, the thickness of the active material 224 is between approximately 0.1 µm and 3 mm. According to other exemplary embodiments, the thickness of the active material 224 may be between approximately 25 µm and 300 µm. According to another exemplary embodiment, the thickness of the active material 224 may be between approximately 20 µm and 90 µm, and according to a particular exemplary embodiment, approximately 75 µm.

Figure 4:
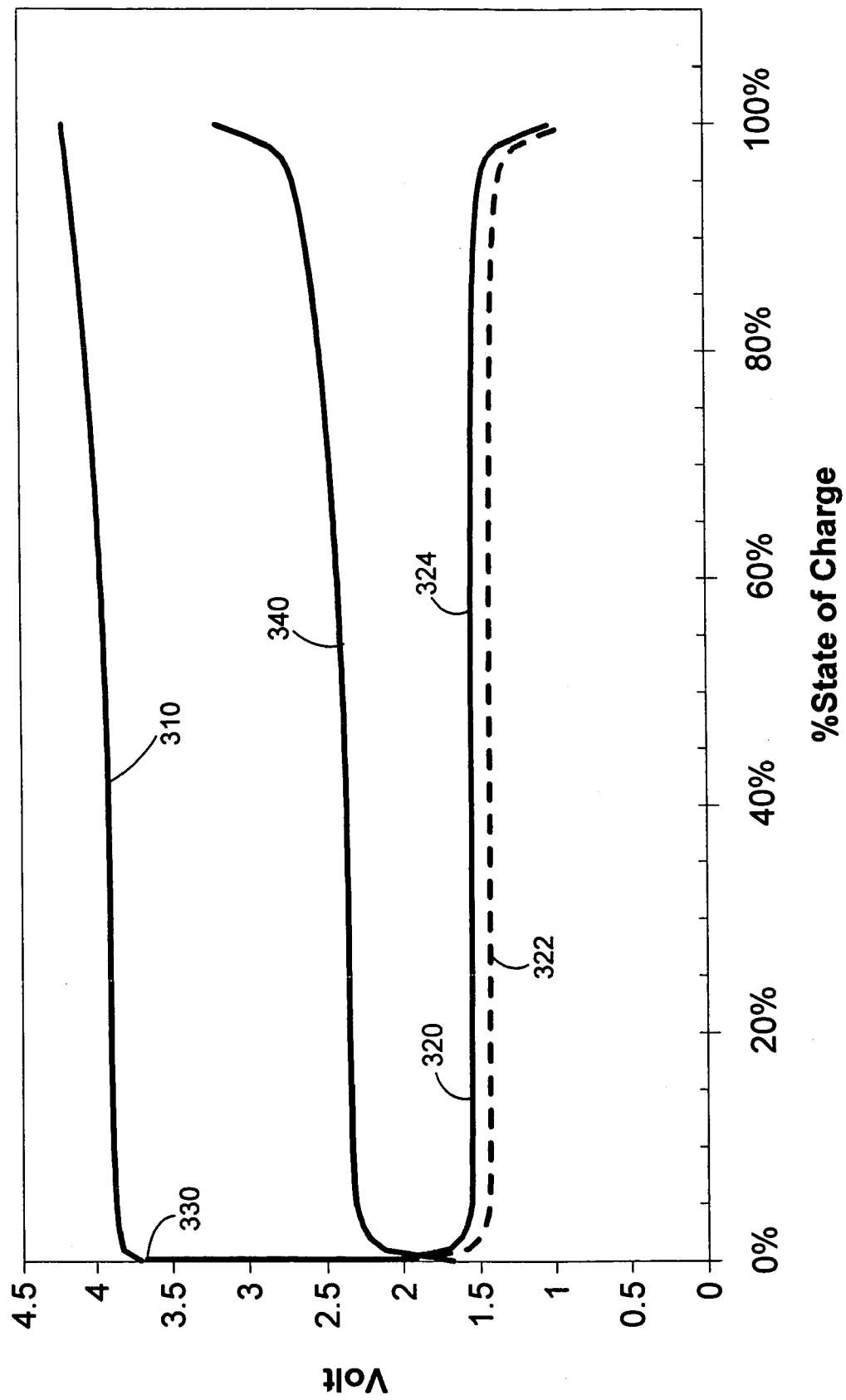
FIG. 4 is a graph illustrating the theoretical charging and discharging behavior for a lithium-ion battery such as that shown in FIG. 3.

FIG. 4 is a graph 300 illustrating the theoretical charging and discharging behavior for a lithium-ion battery constructed in accordance with an exemplary embodiment such as that shown and described with regard to FIG. 3. Curve 310 represents the electrode potential for a positive electrode (e.g., positive electrode 210) that includes an aluminum current collector having a $LiCoO_2$ primary active material provided thereon.

Curve 320 represents the electrode potential for a negative electrode that includes an aluminum current collector having a lithium titanate active material provided thereon. The difference between curves 310 and 320 is representative of the overall cell voltage of the battery, and is represented as curve 340 in FIG. 4.

Figure 1:
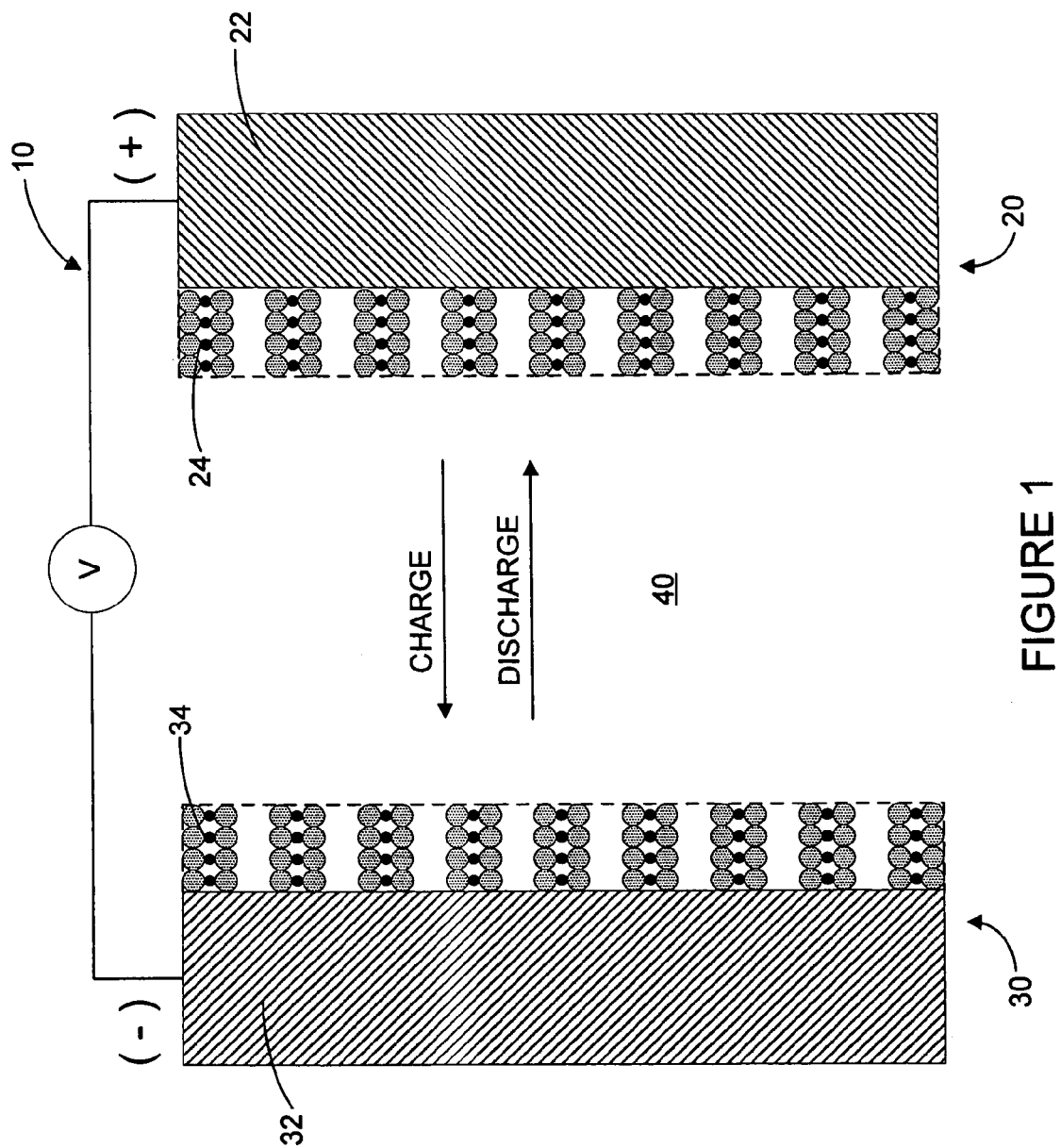
FIG. 1 is a schematic cross-sectional view of a conventional lithium-ion battery.
Figure 2:
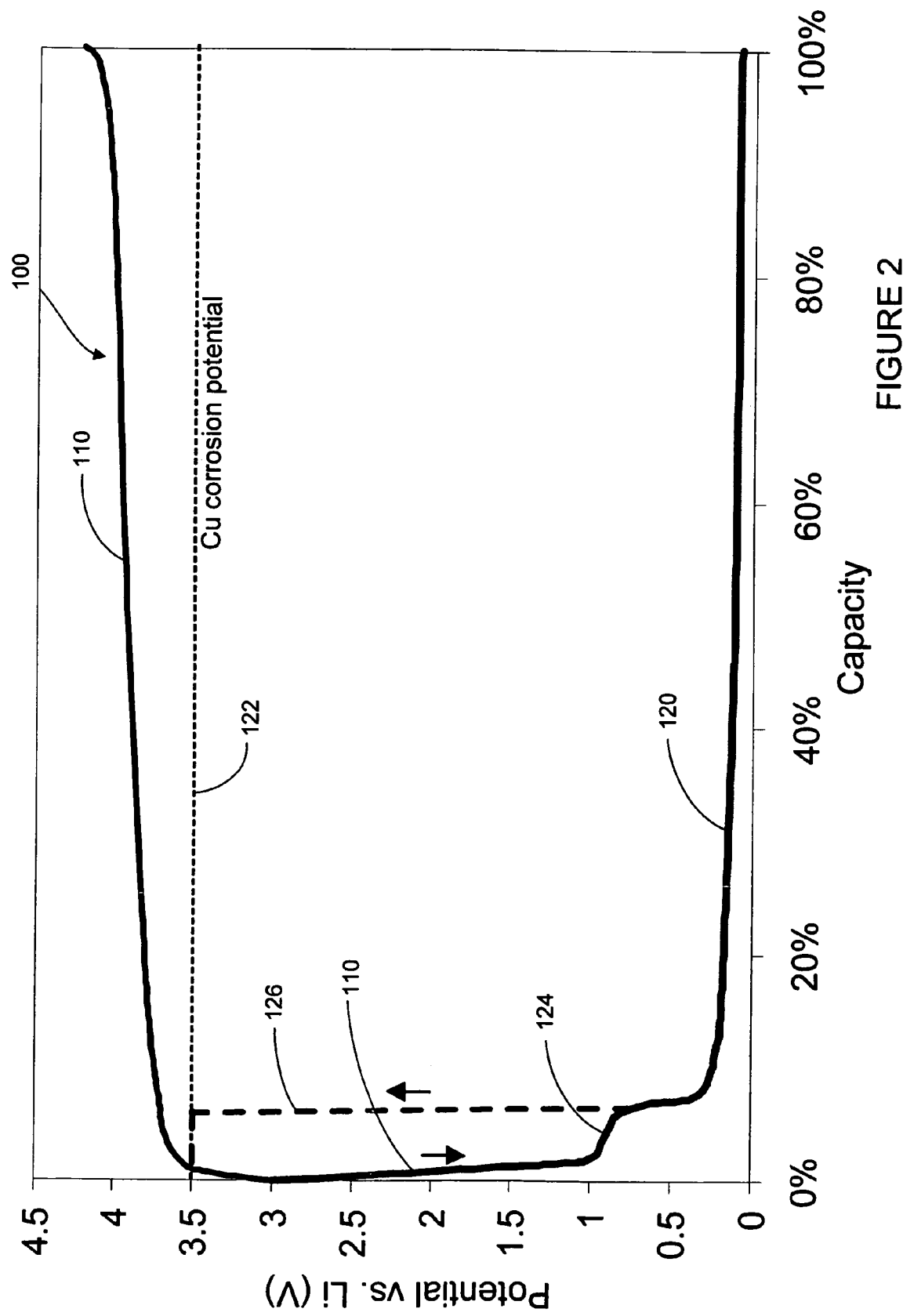
FIG. 2 is a graph illustrating the theoretical charging and discharging behavior for a conventional lithium-ion battery such as that shown schematically in FIG. 1.

As shown in FIG. 4, the relatively flat portion (labeled with reference numeral 324) of the curve 320 representing the voltage of the negative electrode (e.g., electrode 220) is at a level of between approximately 1.5 and 1.6 volts. Thus, the relatively flat portion 324 of the curve 320 is at a level that is significantly greater than that of an electrode utilizing a carbon active material (see, e.g., curve 120 in FIG. 2, which represents the theoretical voltage for a negative electrode incorporating a carbon active material).

One potential advantageous feature of utilizing a lithium titanate material for the negative electrode active material is that more favorable design rules may be possible. For example, in conventional lithium-ion cells, the negative electrode must overlap the positive electrode by approximately 1 mm on all edges in order to avoid plating of lithium. For applications in which space is a concern, this may result in significant wasted volume (e.g., for a cranial implant cell that is approximately 22 mm high, this may result in wasted volume of approximately 10 percent). Because use of a titanate material reduces the risk of lithium plating, it is believed that the design requirement of overlapping positive and negative electrodes may be unnecessary, thus allowing the production of lithium-ion batteries with improved energy density.

The lithium diffusion coefficient for lithium titanate materials may be on the order of approximately $2 \times 10^{-8}$ cm$^2$/s, which is approximately ten times that of carbon, thus allowing a comparatively rapid sustained rate capability. The use of such materials may allow the manufacture of batteries having lower surface area electrodes while still achieving adequate power and recharge rates. According to an exemplary embodiment, a battery utilizes monolithic (i.e., single-plate) electrodes in a coin cell or a foil laminate package. Due to the comparatively rapid sustained rate capability of the lithium titanate material, the battery may be relatively thin (e.g., approximately 1 mm) and inexpensive. Further, according to other exemplary embodiments, batteries may be produced in contoured shapes, which may allow for packaging of such batteries unobtrusively and in unconventional ways in a device (such as along an inner surface of a device housing or case such as a housing for a medical device such as a pacemaker). This may be especially advantageous in a device such as a cranial implant, where it may be desirable to provide the device having a contour to match the curvature of the skull.

Conventional lithium-ibn cells are balanced with a nominal excess negative active material of between approximately five and ten percent to avoid plating of lithium. The use of excess active material results in a larger battery, which results in a cell having reduced energy density. According to an exemplary embodiment, a battery or cell using a lithium titanate active material on an aluminum negative current collector may be produced without excess negative active material (e.g., as a "balanced design").

Another advantageous feature of using a lithium titanate material is that it is believed that when used in a negative electrode of a lithium-ion battery, such materials will cycle lithium at a potential plateau of about 1.55 volts (see, e.g., FIG. 4, which shows as curve 324 the potential of the negative electrode at a level of approximately 1.5 volts during charging of the battery between approximately 3% and 90% state of charge). This is substantially higher than graphitic carbon, which cycles lithium at approximately 0.1 volts in the fully charged state (see, e.g., FIG. 2, in which curve 120 is representative of the charging/discharging behavior of a negative electrode utilizing graphitic carbon).

Because such lithium-ion batteries cycle lithium at a plateau of about 1.55 volts, they are believed to be less susceptible to lithium plating. Lithium plating is a well-known phenomenon that can lead to loss in performance of lithium ion batteries. Lithium-ion batteries using lithium titanate as negative active material are believed to be less likely to result in plating of lithium (which occurs at 0 volts versus a lithium reference) while being charged. For example, lithium batteries using lithium titantate negative active material may be charged such that, at one or more points in a charging operation, the potential of the negative electrode is more than 70 millivolts lower than its equilibrium (i.e., open circuit) potential. Dashed curve 322 shown in FIG. 4 represents a potential for the negative electrode that is approximately 70 millivolts below the equilibrium potential of the negative electrode (shown as curve 324). Charging a lithium-ion battery such as that described herein in a manner that causes the potential of the negative electrode to fall between curve 322 and zero volts versus a lithium reference electrode (e.g., in a range between curve 322 and the x-axis of the graph in FIG. 4) will not result in plating of lithium, whereas a conventional lithium-ion battery having a carbonaceous negative electrode would likely plate lithium at such a potential.

Another advantage of using a lithium titanate material instead of a carbonaceous material for the negative active material is that it is believed that the use of a lithium titanate material allows for charging and discharging of the battery at higher rates than is capable using carbonaceous materials. For example, a common upper limit for the rate of charge in lithium ion batteries is about 1 C (meaning that the battery can be fully charged from the discharged state in one hour). Conversely, it has been reported in literature that lithium titanate may be charged at rates up to 10 C (i.e., attaining full charge in 1/10 hour, or six minutes). One potential reason for this is that negative electrodes utilizing a lithium titanate active material are believed to be less susceptible to the risk of lithium plating. The ability to recharge a battery more quickly may substantially increase the functionality of devices that employ such a battery.

It is also believed that the use of negative electrodes that include a lithium titanate active material may allow for charging of the battery at voltages that exceed those used in the charging of batteries in which the negative electrodes utilize carbon active materials. One potential advantage of such a property is that nonhermetic cells (e.g., cells using a rivet polymer feedthrough, foil package, etc.) may be produced. Nonhermetic cells typically have greater energy density than other cells, are relatively inexpensive to manufacture, and may be produced using a wider variety of materials (e.g, polymer foil laminates, etc.). In medical applications in particular, such cells have conventionally utilized with polymer or gel electrolytes which have lower vapor pressure to provide a reduced risk of leakage. However, such electrolytes are typically less conductive than liquid electrolytes, resulting in relatively low power and/or charge rate. By utilizing a battery that includes a lithium titanate active material on an aluminum current collector, the charge voltage of the cell may be increased to compensate for resistive losses (e.g., an IR drop) in the electrolyte.

Because of the various potentially advantageous features described above for batteries utilizing a lithium titanate negative active material (e.g., provided on an aluminum negative current collector and used with a positive electrode having an active material such as $LiCoO_2$ provided thereon), it is believed that a number of charging routines may be used that may not otherwise be utilized with conventional lithium-ion batteries (e.g., batteries that do not use a lithium titantate negative active material). Non-exclusive exemplary embodiments of such charging routines are illustrated in FIGS. 5-10. Each of such charging routines causes the potential of the negative electrode (with reference to a lithium electrode) to be more than approximately 70 millivolts below the equilibrium (e.g., open circuit) potential of that electrode for at least a portion of the charging operation (i.e., the overpotential of the charging is greater than approximately 70 millivolts). The use of lithium titanate active material on the negative electrode allows the potential of the negative electrode to reach this level without plating lithium on the electrode.

Figure 5:
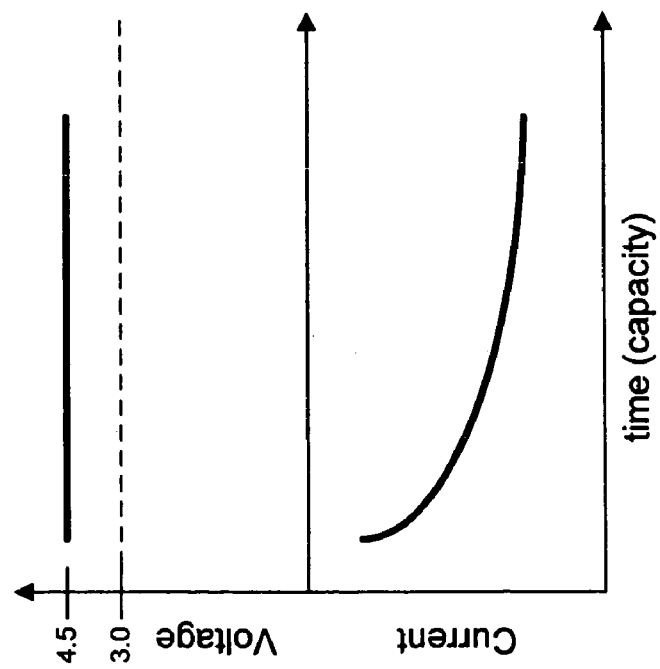
FIG. 5 is a graph illustrating a possible battery charging routine or algorithm according to a theoretical exemplary embodiment.

FIG. 5 is a graph illustrating a theoretical charging routine or algorithm according to an exemplary embodiment. As shown in FIG. 5, a constant voltage charging routine may be utilized in which the charging voltage is controlled at a level that exceeds the final charge voltage of the battery (the charging current correspondingly decreases with increased charging of the battery). For example, according to an exemplary embodiment in which the final charge voltage of the battery (i.e., the open circuit voltage of the fully charged battery) is approximately 3 volts, the battery may be charged at a constant voltage of up to approximately 4.5 volts as shown in FIG. 5. The 1.5 volt difference between the desired final charge voltage and the charging voltage represents the approximate potential of the negative electrode (see, e.g., FIG. 4). This charging routine results in an overpotential of greater than 70 millivolts for at least a portion of the charging operation. In this manner, charging of the battery may be accomplished at a relatively quick rate as compared to charging of batteries using conventional negative electrode materials (e.g., carbon, etc.).

To determine the point at which charging of the battery as shown in FIG. 5 should be terminated, various cutoff criteria may be utilized. As shown in FIG. 4, batteries using lithium titanate active materials on the negative electrode may experience a relatively abrupt increase in cell voltage at the end of charging (see, e.g., the right-most portion of curve 340 in FIG. 4); such an abrupt increase may correspond to a relatively abrupt decrease in negative electrode potential (see, e.g., curve 320 in FIG. 4) that is not generally present in batteries using carbon or other conventional negative active materials (since the potential of the negative electrode at this point is already near zero volts, as shown, for example, in FIG. 2). Identification of this point during charging may be used as an indication that charging is nearly complete and/or that charging should be stopped. Various other techniques may also be used for determining when charging of the battery should be stopped. For example, charging of the battery may be stopped when a predetermined amount of time has elapsed according to an exemplary embodiment. According to another exemplary embodiment, charging of the battery may be stopped when the current of the battery falls below a predetermined threshold (i.e., the current as shown in the lower portion of FIG. 5 may fall below a predetermined threshold value). According to another exemplary embodiment, charging of the battery may be stopped when the slope of the current of the battery with time (i.e., di/dt) falls below a predetermined threshold.

Figure 6:
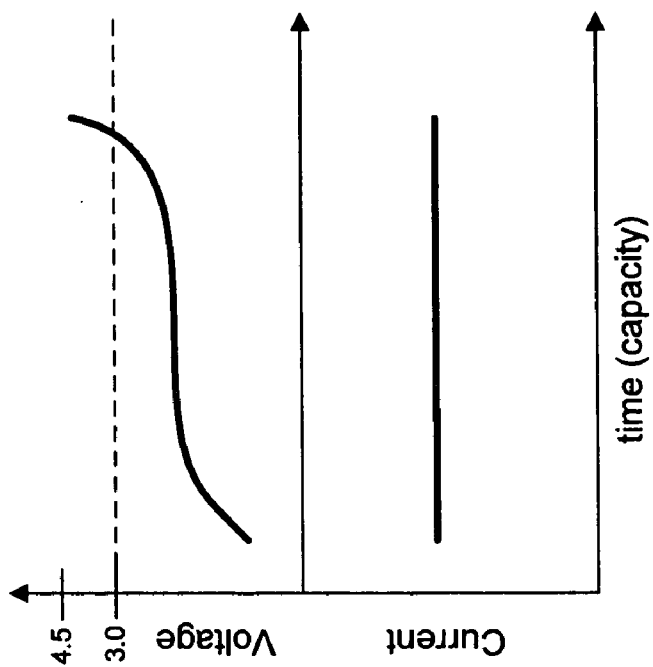
FIG. 6 is another graph illustrating a possible battery charging routine or algorithm according to another theoretical exemplary embodiment.

FIG. 6 is a graph illustrating a theoretical charging routine or algorithm according to another exemplary embodiment. As shown in FIG. 6, a constant current charging routine may be utilized in which the charging current is controlled at a constant level. The charging voltage then proceeds according to a graph similar to that shown in FIG. 6 such that it eventually reaches a level (e.g., 4.5 volts) that exceeds the final charge voltage of the battery (e.g., 3 volts). Again, because of the use of a lithium titanate material as the negative active material, it is believed that lithium plating on the negative electrode may be avoided even though at some point during charging, the overpotential exceeds approximately 70 millivolts. In this manner, charging of the battery may be accomplished at a relatively quick rate as compared to charging of batteries using conventional negative electrode materials (e.g., carbon, etc.).

To determine the point at which charging of the battery as shown in FIG. 6 should be terminated, various cutoff criteria may be utilized. For example, charging of the battery may be stopped when the voltage of the battery exceeds a predetermined threshold (i.e., the voltage as shown in the upper portion of FIG. 6 rises above a predetermined threshold value, such as 4.5 volts). According to another exemplary embodiment, charging of the battery may be stopped when the slope of the voltage of the battery with time (i.e., dV/dt) exceeds a predetermined threshold. According to another exemplary embodiment, charging of the battery may be stopped when the slope of the voltage of the battery versus the capacity of the battery (i.e., dV/dQ) exceeds a predetermined threshold.

Figure 7:
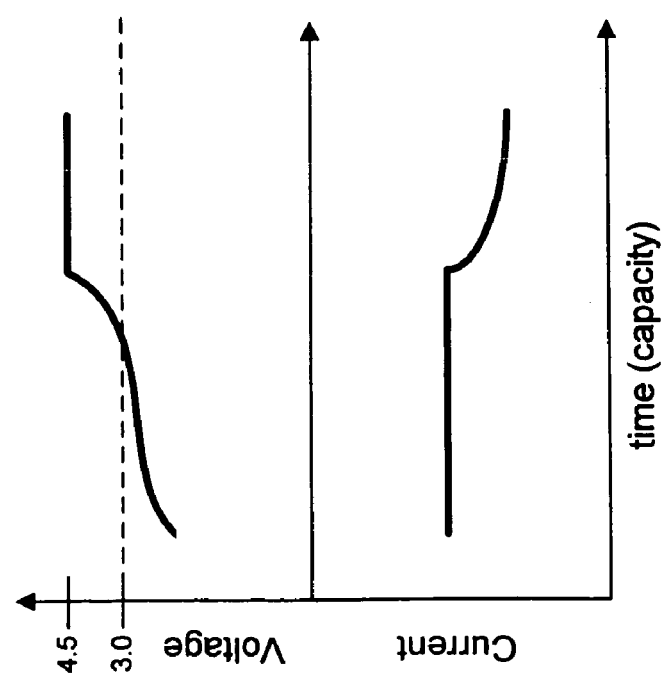
FIG. 7 is another graph illustrating a possible battery charging routine or algorithm according to another theoretical exemplary embodiment.

FIG. 7 is a graph illustrating a theoretical charging routine or algorithm according to another exemplary embodiment that combines portions of the charging routines shown in FIGS. 5 and 6. As shown in FIG. 7, a first portion of the charging routine utilizes a controlled constant current, while a second portion of the charging routine utilizes a controlled constant voltage. For example, the current may be controlled at a constant level to the point at which charging voltage reaches a predetermined threshold above the desired final voltage of the battery (e.g., 4.5 volts), after which the charging voltage is controlled at this threshold value (at which point the current decreases with time as shown in FIG. 7).

To determine the point at which charging of the battery as shown in FIG. 7 should be terminated, various cutoff criteria may be utilized. For example, charging of the battery may be stopped when a predetermined amount of time has elapsed according to an exemplary embodiment. According to another exemplary embodiment, charging of the battery may be stopped when the current of the battery falls below a predetermined threshold.

Figure 8:
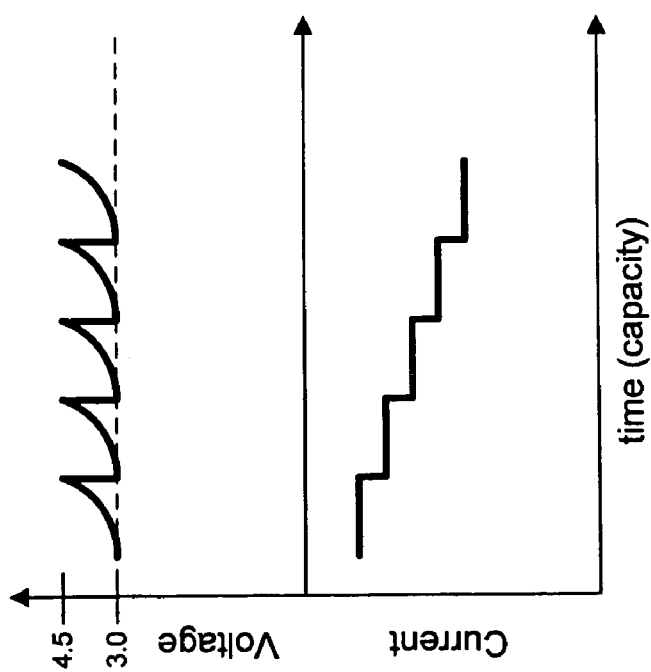
FIG. 8 is another graph illustrating a possible battery charging routine or algorithm according to another theoretical exemplary embodiment.

FIG. 8 is a graph illustrating a theoretical charging routine or algorithm according to another exemplary embodiment in which a step-down current may be utilized. As shown in FIG. 8, the application of a constant current causes the charging voltage to increase to a predetermined threshold (e.g., 4.5 volts). Upon reaching this charging voltage, the current is stepped down to a lower constant current value. This process is repeated such that the current is stepped down to a lower constant value each time the charging voltage approaches the predetermined threshold (or a different threshold value according to another exemplary embodiment).

To determine the point at which charging of the battery as shown in FIG. 8 should be terminated, various cutoff criteria may be utilized. For example, charging of the battery may be stopped when a predetermined amount of time has elapsed according to an exemplary embodiment. According to another exemplary embodiment, charging of the battery may be stopped when a predetermined number of steps (e.g., step downs in charging current) have been taken. According to another exemplary embodiment, charging of the battery may be stopped when the current of the battery falls below a predetermined threshold (e.g., charging stops when the current value is stepped down to a level below the predetermined threshold). According to another exemplary embodiment, charging of the battery may be stopped when a change in voltage associated with a given current level is below a predetermined value (e.g., for a particular charging current, the drop in voltage is below a predetermined threshold).

Figure 10:
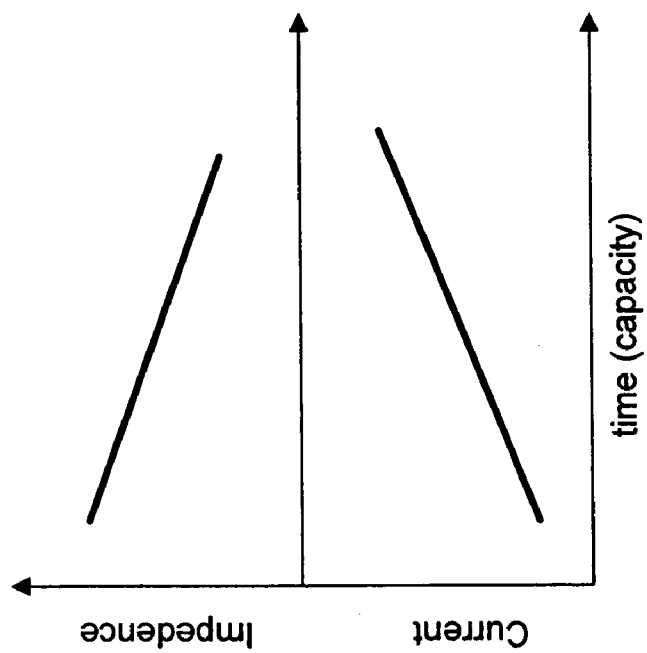
FIG. 10 is another graph illustrating a technique for determining the impedence or resistance of a battery during a charging routine or algorithm according to an exemplary embodiment.
Figure 9:
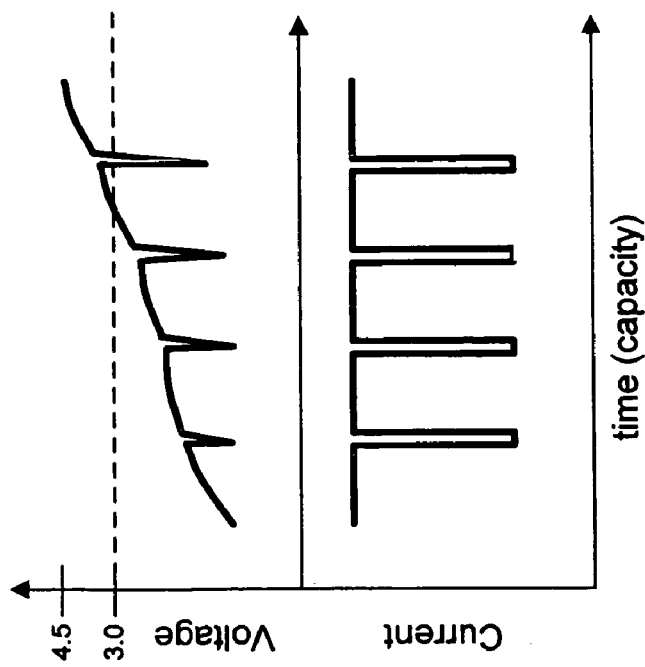
FIG. 9 is a graph illustrating a possible battery charging routine or algorithm according to another theoretical exemplary embodiment.

FIGS. 9 and 10 illustrate techniques that may be used with the routines or algorithms shown in FIGS. 5-8. FIG. 9 illustrates the use of a current interruption technique in conjunction with a charging routine or algorithm similar to that shown in FIG. 6. At periodic intervals during charging, the charging current is removed according to an exemplary embodiment (e.g., no current is applied). According to another exemplary embodiment, the periodic current interruption may be provided as a drop in current (as opposed to complete removal of the current). Periodic removal or reduction of the current causes a relatively instantaneous drop in the voltage; this voltage drop may be read to determine the open circuit voltage of the battery at a given point in time. Once the open circuit voltage is determined to have a value approaching the desired final battery voltage, the charging routine may be stopped.

FIG. 10 illustrates the use of an algorithm or routine in which the resistance or impedance of the battery is periodically measured during charging of the battery to prevent the overvoltage (the difference between the charging voltage and the desired final battery voltage) from exceeding a predetermined threshold value (e.g., 1.5 volts, which as shown in FIG. 4, corresponds to the approximate potential of the negative electrode). In this manner, charging of the battery at a voltage above the desired final battery voltage may proceed with a reduced risk that the overvoltage will exceed a threshold at which it is believed that lithium plating of the negative electrode may occur.

It should be noted that similar techniques to those shown and described with respect to FIGS. 9-10 may be used with the other routines or algorithms shown and described with respect to FIGS. 5-8. For example, the impedance or resistance of the battery may be measured in conjunction with any of the routines to ensure that the overvoltage of the charging routine does not exceed a threshold at which lithium plating may occur. Similarly, either voltage or current interruption techniques may be utilized to obtain a relatively instantaneous measurement of the open circuit voltage of the battery being charged.

While FIGS. 9-10 illustrate charging routines that are interrupted during the charging operation, it should be noted that because a lithium titanate material is utilized as the negative active material, such interruptions or suspensions in the charging operation may be omitted since the risk of plating lithium is less for these batteries than for conventional lithium ion batteries using a carbonaceous active material.

It should be noted that the routines or algorithms shown and described with respect to FIGS. 5-10 contemplate charging at an overpotential during charging of the batteries for at least a portion of the charging operation. While the embodiments shown and described have utilized a threshold overpotential of approximately 70 millivolts, it should be noted that any suitable overpotential may be used according to various exemplary embodiments, so long as plating of lithium is avoided. For example, overpotentials of greater than 100 millivolts may be used according to other exemplary embodiments. The use of lithium titanate negative active materials may advantageously allow the use of overpotentials during charging that may not otherwise be utilized with batteries utilizing conventional negative active materials (e.g., carbon) due to lithium plating that may occur in such batteries.

EXAMPLE

Single plate lithium ion cells with a reference electrode were fabricated in stainless steel cans. The positive electrode comprised a coating of $LiCoO_2$, powdered graphite and PVDF on an aluminum current collector. The negative electrode consisted of a coating of $Li_4Ti_5O_{12}$, carbon black, and PVDF on an aluminum foil current collector. The $Li_4Ti_5O_{12}$ was obtained under the trade name "EXM 1037", commercially available from Sud-Chemie of Munich, Germany). The $Li_4Ti_5O_{12}$ included about 40 volume percent of particles less than 500 nm, as measured by laser diffraction. The mass deposition of the positive coating was about 22 $mg/cm^2$, and the calendered thickness of the coating was about 70 microns. The mass deposition of the negative electrode was about 17 $mg/cm^2$ and the calendared thickness was about 75 microns. The electrode active area was about 5 $cm^2$.

The reference electrode consisted of a nugget of metallic lithium on the end of a feedthrough pin, placed in the headspace of the cell. Cells were activated using an electrolyte consisting of a 1 M $LiPF_6$ in a mixture of propylene carbonate, ethylene carbonate and diethyl carbonate. The cell was formed and cycled using an ARBIN BT-2000 battery cycler at 37° C. During cycling, the current, the cell voltage and potential of the negative electrode versus the Li reference electrode were monitored. After completion of twelve conditioning cycles, the battery underwent two cycles to compare the charge rate under a constant current (0.5 mA) and constant voltage (3 V) charging condition.

Figure 11:
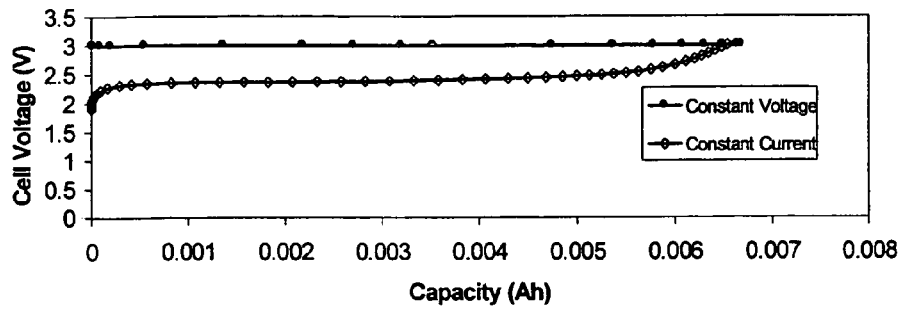
FIGS. 11A-D are graphs illustrating the charging performance of a battery according to an exemplary embodiment.
Figure 11:
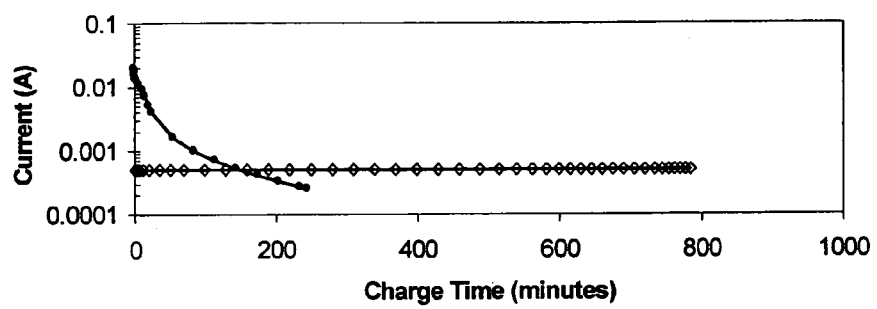
Figure 11:
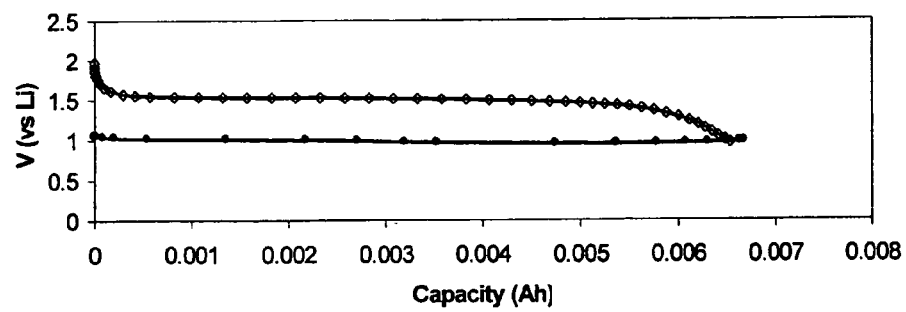
Figure 11:
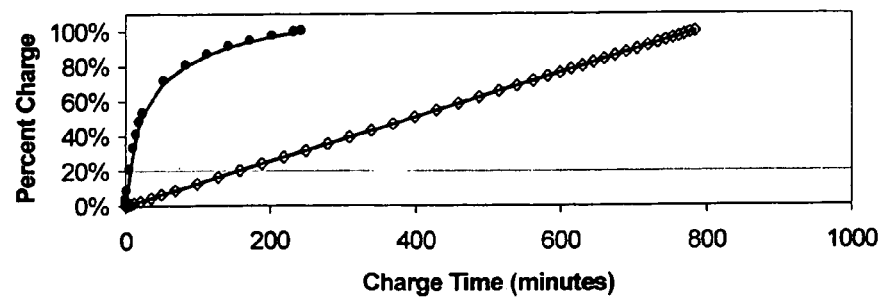

FIGS. 11A-D illustrate a comparison of results for constant current and constant charge conditions. The cell voltage, charge current, negative electrode potential and percent charge are shown in FIGS. 11A, 11B, 11C, and 11D, respectively. The constant voltage charge condition resulted in the cell being charged at a much greater rate than in the constant current condition. For example, as shown in FIG. 11D, the cell reached 80% of full charge in about 84 minutes when charged at constant voltage, compared to 10% for the constant current condition. As shown in FIG. 11C, the potential of the negative electrode during constant voltage charge was approximately 500 mV lower during the constant voltage charge than in the constant current charge condition. This indicates that the overvoltage or overpotential of the negative electrode was at least 500 mV during the constant voltage charge. By using this relatively large overpotential during the charging operation, the cell was able to be charged in a substantially shorter time as compared to the charging operation that did not utilize such an overpotential.

According to an exemplary embodiment, lithium-ion batteries and charging rountines such as those described above may be used in conjunction with medical devices such as medical devices that may be implanted in the human body (referred to as "implantable medical devices" or "IMDs"). One advantage of using lithium-ion batteries and charging routines such as those described herein with IMDs is that the relatively quick charge times may act to reduce the potential inconvenience to the patient.

Figure 12:
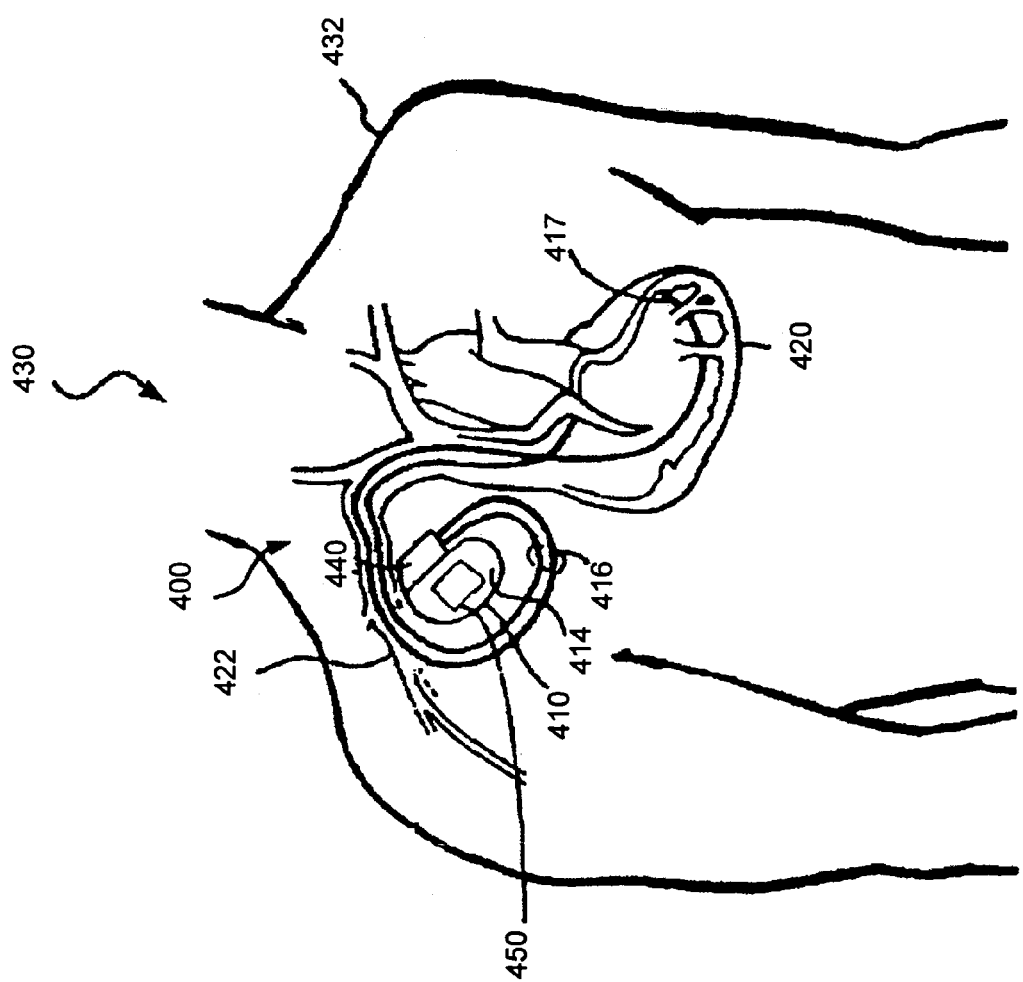
FIG. 12 is a schematic view of a system in the form of an implantable medical device implanted within a body or torso of a patient.

FIG. 12 illustrates a schematic view of a system 400 (e.g., an implantable medical device) implanted within a body or torso 432 of a patient 430. The system 400 includes a device 410 in the form of an implantable medical device that for purposes of illustration is shown as a defibrillator configured to provide a therapeutic high voltage (e.g., 700 volt) treatment for the patient 430.

The device 410 includes a container or housing 414 that is hermetically sealed and biologically inert according to an exemplary embodiment. The container may be made of a conductive material. One or more leads 416 electrically connect the device 410 and to the patient's heart 420 via a vein 422. Electrodes 417 are provided to sense cardiac activity and/or provide an electrical potential to the heart 420. At least a portion of the leads 416 (e.g., an end portion of the leads shown as exposed electrodes 417) may be provided adjacent or in contact with one or more of a ventricle and an atrium of the heart 420.

The device 410 includes a battery 440 provided therein to provide power for the device 410. According to another exemplary embodiment, the battery 440 may be provided external to the device or external to the patient 430 (e.g., to allow for removal and replacement and/or charging of the battery). The size and capacity of the battery 440 may be chosen based on a number of factors, including the amount of charge required for a given patient's physical or medical characteristics, the size or configuration of the device, and any of a variety of other factors. According to an exemplary embodiment, the battery is a 5 mAh battery. According to another exemplary embodiment, the battery is a 300 mAh battery. According to various other exemplary embodiments, the battery may have a capacity of between approximately 1 and 1000 mAh.

According to other exemplary embodiments, more than one battery may be provided to power the device 410. In such exemplary embodiments, the batteries may have the same capacity or one or more of the batteries may have a higher or lower capacity than the other battery or batteries. For example, according to an exemplary embodiment, one of the batteries may have a capacity of approximately 500 mAh while another of the batteries may have a capacity of approximately 75 mAh.

Figure 13:
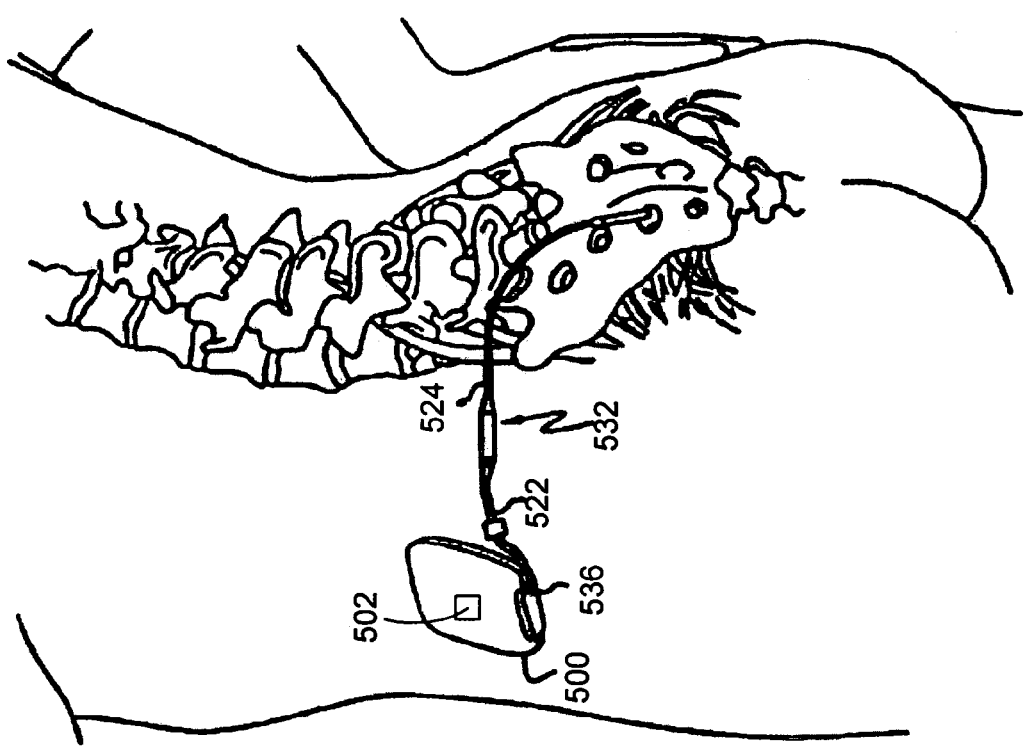
FIG. 13 is schematic view of another system in the form of an implantable medical device.

According to another exemplary embodiment shown in FIG. 13, an implantable neurological stimulation device 500 (an implantable neuro stimulator or INS) may include a battery 502 such as those described above with respect to the various exemplary embodiments. Examples of some neuro stimulation products and related components are shown and described in a brochure titled "Implantable Neurostimulation Systems" available from Medtronic, Inc.

An INS generates one or more electrical stimulation signals that are used to influence the human nervous system or organs. Electrical contacts carried on the distal end of a lead are placed at the desired stimulation site such as the spine or brain and the proximal end of the lead is connected to the INS. The INS is then surgically implanted into an individual such as into a subcutaneous pocket in the abdomen, pectoral region, or upper buttocks area. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea. Additional therapies appear promising to treat a variety of physiological, psychological, and emotional conditions. Before an INS is implanted to deliver a therapy, an external screener that replicates some or all of the INS functions is typically connected to the patient to evaluate the efficacy of the proposed therapy.

The INS 500 includes a lead extension 522 and a stimulation lead 524. The stimulation lead 524 is one or more insulated electrical conductors with a connector 532 on the proximal end and electrical contacts (not shown) on the distal end. Some stimulation leads are designed to be inserted into a patient percutaneously, such as the Model 3487A Pisces-Quad® lead available from Medtronic, Inc. of Minneapolis Minn., and stimulation some leads are designed to be surgically implanted, such as the Model 3998 Specify® lead also available from Medtronic.

Although the lead connector 532 can be connected directly to the INS 500 (e.g., at a point 536), typically the lead connector 532 is connected to a lead extension 522. The lead extension 522, such as a Model 7495 available from Medtronic, is then connected to the INS 500.

Implantation of an INS 520 typically begins with implantation of at least one stimulation lead 524, usually while the patient is under a local anesthetic. The stimulation lead 524 can either be percutaneously or surgically implanted. Once the stimulation lead 524 has been implanted and positioned, the stimulation lead's 524 distal end is typically anchored into position to minimize movement of the stimulation lead 524 after implantation. The stimulation lead's 524 proximal end can be configured to connect to a lead extension 522.

The INS 500 is programmed with a therapy and the therapy is often modified to optimize the therapy for the patient (i.e., the INS may be programmed with a plurality of programs or therapies such that an appropriate therapy may be administered in a given situation). In the event that the battery 502 requires recharging, an external lead (not shown) may be used to electrically couple the battery to a charging device or apparatus.

A physician programmer and a patient programmer (not shown) may also be provided to allow a physician or a patient to control the administration of various therapies. A physician programmer, also known as a console programmer, uses telemetry to communicate with the implanted INS 500, so a clinician can program and manage a patient's therapy stored in the INS 500, troubleshoot the patient's INS 500 system, and/or collect data. An example of a physician programmer is a Model 7432 Console Programmer available from Medtronic. A patient programmer also uses telemetry to communicate with the INS 500, so the patient can manage some aspects of her therapy as defined by the clinician. An example of a patient programmer is a Model 7434 Itrel® 3 EZ Patient Programmer available from Medtronic.

While the medical devices described herein (e.g., systems 400 and 500) are shown and described as a defibrillator and a neurological stimulation device, it should be appreciated that other types of implantable medical devices may be utilized according to other exemplary embodiments, such as pacemakers, cardioverters, cardiac contractility modules, drug administering devices, diagnostic recorders, cochlear implants, and the like for alleviating the adverse effects of various health ailments. According to still other embodiments, non-implantable medical devices or other types of devices may utilize batteries as are shown and described in this disclosure.

It is also contemplated that the medical devices described herein may be charged or recharged when the medical device is implanted within a patient. That is, according to an exemplary embodiment, there is no need to disconnect or remove the medical device from the patient in order to charge or recharge the medical device. For example, transcutaneous energy transfer (TET) may be used, in which magnetic induction is used to deliver energy from outside the body to the implanted battery, without the need to make direct physical contact to the implanted battery, and without the need for any portion of the implant to protrude from the patient's skin.

According to another exemplary embodiment, a connector may be provided external to the patient's body that may be electrically coupled to a charging device in order to charge or recharge the battery. According to other exemplary embodiments, medical devices may be provided that may require removal or detachment from the patient in order to charge or recharge the battery.

Another application in which the use of batteries such as those described herein may be in multiple-battery systems in which two or more batteries are used (e.g., as a power module for the multiple-battery device). An example of this would be an implantable cardioverter defibrillator (ICD) which contains two batteries. ICD's operate over most of their lifetime in a low-power mode but must supply relatively high power (e.g., 10 watts) for periods of a few seconds each when a defibrillation shock is needed. A low or medium rate primary cell (for example a lithium battery with a cathode consisting of $CF_x$, $CF_x$-SVO hybrid, or lithium/$MnO_2$) acts as the energy module, supplying the majority of the energy to the device. However, the energy module is incapable of sustaining high power. It is therefore connected in parallel to the lithium ion cell such as that disclosed herein (e.g., a battery having a lithium titanate active material provided on an aluminum, silver, or titanium negative current collector and a positive electrode having an active material such as those described herein provided thereon), which acts as the power module during high drain applications. The combined two-cell battery has both high energy and power density. When connecting two cells in parallel, it is essential that the two cell voltages are compatible with each other. With a standard lithium ion cell, the voltage is too high (about 3.7 V) to be connected in parallel with most lithium primary cells. Doing so would result in damage to the primary cells and possibly harm to the patient. However, utilizing a lithium ion cell such as that disclosed herein may allow for a relatively safe connection to a lithium primary cell as the voltage ranges of the two cell types overlap perfectly.

It is important to note that the construction and arrangement of the lithium-ion battery as shown and described with respect to the various exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. Accordingly, all such modifications are intended to be included within the scope of the present invention as defined in the appended claims. Other substitutions, modifications, changes and omissions may be made in the design, operating conditions and arrangement of the preferred and other exemplary embodiments without departing from the scope of the present invention.

What is claimed is:

1. A method for charging an implantable medical device comprising:
    charging a lithium-ion battery provided in a medical device, the lithium-ion battery having a negative electrode with a lithium titanate active material;
    wherein for at least a portion of the charging, the potential of the negative electrode is more than approximately 70 millivolts below the equilibrium potential of the negative electrode.

2. The method of claim 1, wherein for at least a portion of the charging, the potential of the negative electrode is more than approximately 100 millivolts below the equilibrium potential of the negative electrode.

3. The method of claim 1, wherein the step of charging the lithium-ion battery maintains the potential of the negative electrode above zero volts compared to a lithium reference electrode.

4. The method of claim 1, wherein the step of charging the lithium-ion battery is part of a charging operation that utilizes a constant charging voltage.

5. The method of claim 1, wherein the step of charging the lithium-ion battery is part of a charging operation that utilizes a constant charging current.

6. The method of claim 1, wherein the step of charging the lithium-ion battery is part of a charging operation in which a first portion of the charging operation utilizes a constant charging current and a second portion of the charging operation utilizes a constant charging voltage.

7. The method of claim 1, wherein the step of charging the lithium-ion battery is part of a charging operation that utilizes a step-down current method.

8. The method of claim 1, further comprising terminating the charging of the lithium-ion battery when a predetermined condition is met, the predetermined condition selected from the group consisting of (a) an abrupt decrease in negative electrode potential, (b) the passing of a predetermined amount of time, (c) the current of the lithium-ion battery falling below a predetermined threshold, and (d) the slope of the current of the lithium-ion battery with time (di/dt) falling below a predetermined threshold.

9. The method of claim 1, further comprising terminating the charging of the lithium-ion battery when a predetermined condition is met, the predetermined condition selected from the group consisting of (a) the voltage of the lithium-ion battery exceeding a predetermined threshold, (b) the slope of the voltage of the lithium-ion battery with time (dV/dt) exceeding a predetermined threshold, and (c) the slope of the voltage of the lithium-ion battery with capacity (dV/dQ) exceeding a predetermined threshold.

10. The method of claim 1, wherein the lithium-ion battery comprises a positive electrode comprising a current collector and an active material comprising a material selected from the group consisting of $LiCoO_2$, $LiMn_2O_4$, $LiMn_xCo_yNi_{(1-x-y)}O_2$, $LiAl_xCo_yNi_{(1-x-y)}O_2$, $LiTi_xCo_yNi_{(1-x-y)}O_2$, and combinations thereof.

11. The method of claim 1, wherein the negative electrode comprises a current collector comprising a material selected from the group consisting of aluminum, titanium, silver, and combinations thereof.

12. The method of claim 1, wherein the lithium titanate active material comprises $Li_4Ti_5O_{12}$.

13. The method of claim 1, wherein the lithium titanate active material comprises at least five percent nanoparticles.

14. The method of claim 1, wherein the step of charging the battery is performed with the medical device implanted in a patient.

15. The method of claim 14, wherein the medical device is selected from the group consisting of a neurological stimulation device, a cardiac defibrillator, a cardiac pacemaker, a cardiac contractility module, a cardiac contractility modulator, a cardioverter, a drug administration device, a cochlear implant, a hearing aid, a sensor, a telemetry device, and a diagnostic recorder.

16. The method of claim 15, wherein the step of charging the battery utilizes inductive charging.

17. The method of claim 1, wherein the lithium-ion battery has a positive electrode that has a potential that is greater than approximately 2.8 volts.

18. The method of claim 1, wherein the voltage of the lithium-ion battery is greater than approximately 1.3 volts.

19. The method of claim 1, wherein the lithium-ion battery has a capacity between approximately 1 mAh and 1000 mAh.

20. The method of claim 1, wherein the step of charging the lithium-ion battery is not suspended during charging to determine the state of charge or equilibrium voltage of the lithium-ion battery.

21. A method of charging a lithium-ion battery comprising:
charging a lithium-ion battery in a charging operation, the lithium-ion battery including a negative electrode that comprises a lithium titanate material;
wherein for at least a portion of the charging operation the overpotential of the negative electrode is greater than approximately 70 millivolts;
wherein the lithium battery is included in an implantable medical device and the charging operation does not result in lithium plating at the negative electrode.

22. The method of claim 21, wherein for at least a portion of the charging operation the overpotential of the negative electrode is greater than approximately 100 millivolts.

23. The method of claim 21, wherein the battery has a capacity between approximately 1 mAh and 1000 mAh.

24. The method of claim 21, wherein the charging operation utilizes a constant charging voltage.

25. The method of claim 21, wherein the charging operation utilizes a constant charging current.

26. The method of claim 21, further comprising terminating the charging operation when a predetermined condition is met, the predetermined condition selected from the group consisting of (a) an abrupt decrease in negative electrode potential, (b) the passing of a predetermined amount of time, (c) the current of the lithium-ion battery falling below a predetermined threshold, and (d) the slope of the current of the lithium-ion battery with time (di/dt) falling below a predetermined threshold.

27. The method of claim 21, further comprising terminating the charging operation when a predetermined condition is met, the predetermined condition selected from the group consisting of (a) the voltage of the lithium-ion battery exceeding a predetermined threshold, (b) the slope of the voltage of the lithium-ion battery with time (dV/dt) exceeding a predetermined threshold, and (c) the slope of the voltage of the lithium-ion battery with capacity (dV/dQ) exceeding a predetermined threshold.

28. The method of claim 21, wherein the negative electrode comprises a current collector comprising a material selected from the group consisting of aluminum, titanium, silver, and combinations thereof.

29. The method of claim 21, wherein the lithium titanate active material comprises $Li_4Ti_5O_{12}$.

30. The method of claim 21, wherein the medical device is selected from the group consisting of a neurological stimulation device, a cardiac defibrillator, a cardiac pacemaker, a cardiac contractility module, a cardiac contractility modulator, a cardioverter, a drug administration device, a cochlear implant, a hearing aid, a sensor, a telemetry device, and a diagnostic recorder.

31. The method of claim 21, wherein the charging operation is performed while the medical device is implanted in a patient.

32. A method of charging a lithium-ion battery comprising:
inductively charging a lithium-ion battery according to a charging routine that provides an overpotential of at least 70 millivolts to a negative electrode of the battery for at least a portion of the charging routine, the lithium-ion battery comprising a lithium titanate negative active material.

33. The method of claim 32, wherein the lithium-ion battery has a capacity between approximately 1 mAh and 1000 mAh.

34. The method of claim 33, wherein the charging routine provides an overpotential of at least 100 millivolts to the negative electrode.

35. The method of claim 32, wherein the charging operation utilizes at least one of a constant charging voltage and a constant charging current.

36. The method of claim 32, wherein the negative electrode comprises a current collector comprising a material selected from the group consisting of aluminum, titanium, and silver.

37. The method of claim 32, wherein the lithium-ion battery is provided in a medical device implanted in a patient, the medical device selected from the group consisting of a neurological stimulation device, a cardiac defibrillator, a cardiac pacemaker, a cardiac contractility module, a cardiac contractility modulator, a cardioverter, a drug administration device, a cochlear implant, a hearing aid, a sensor, a telemetry device, and a diagnostic recorder.

38. The method of claim 32, wherein the lithium titanate active material comprises $Li_4Ti_5O_{12}$.

* * * * *

UNITED STATES PATENT AND TRADEMARK OFFICE
CERTIFICATE OF CORRECTION

PATENT NO. : 7,635,541 B2  Page 1 of 1
APPLICATION NO. : 11/260853
DATED : December 22, 2009
INVENTOR(S) : Scott et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1063 days.

Signed and Sealed this

Ninth Day of November, 2010

David J. Kappos
*Director of the United States Patent and Trademark Office*